(12) United States Patent
Shyjan

(10) Patent No.: US 6,890,713 B1
(45) Date of Patent: May 10, 2005

(54) MULTIDRUG RESISTANCE-ASSOCIATED POLYPEPTIDE

(75) Inventor: Andrew Shyjan, Nahant, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/528,031

(22) Filed: Mar. 17, 2000

Related U.S. Application Data

(63) Continuation of application No. 09/061,400, filed on Apr. 16, 1998, now Pat. No. 6,077,936, which is a continuation-in-part of application No. 08/843,459, filed on Apr. 16, 1997, now Pat. No. 6,162,616.

(51) Int. Cl.⁷ .............................................. C12Q 1/68
(52) U.S. Cl. .......................... 435/6; 435/7.2; 435/69.1; 435/70.1; 436/63; 436/64
(58) Field of Search ............................ 435/6, 7.2, 69.1, 435/70.1, 71.1; 436/63, 64

(56) References Cited

FOREIGN PATENT DOCUMENTS

| WO | WO 94/10303 | 5/1994 |
| WO | WO 95/10938 | 4/1995 |
| WO | WO 97/31111 | 8/1997 |

OTHER PUBLICATIONS

Solary et al. Leukemia 5/7:592–597, Jul. 1991.*
Sachs et al., The Journal of Biological Chemistry 270/44:26639–26648, 1995.*
Chao. Environmental Toxicology and Pharmacology 1:63–72, 1996.*
Kool et al. Accession No. U83661, GemEmbl Database, Jan. 3, 1997.*
Raymond et al. Molecular and Cellular Biology 14/1:277–286, 1994.*
Wilson, R. et al. "2.2 Mb of contiguous nucleotide sequence from chromosome III of C. elegans" *Nature* 368:32–38 (GenBank Accession No. Q19048) (1994).
Suzuki, T., et al., "cDNA cloning of a short type of multidrug resistance protein homologue, SMRP, from a human lung cancer cell line" *Biochemical and Biophysical Research Communications* 238(3):790–4 (1997).
Kool, M., et al., " Four homologs of the multidrug resistance protein MRP1" *Eighty–Eighth Annual Meeting of the American Association for Cancer Research,* San Diego, CA, Apr. 12–15, 1997, *Proceedings of the American Association for Cancer Research Annual Meeting,* 38(0), (1997), abstract #2941.

Genbank® Accession Number H17207 for ym42a06.r1 Soares infant brain 1NIB *Homo sapiens* cDNA clone 50857 5' similar to SP:MRP_Human P33527 Multidrug Resistance–Associated; mRNA sequence.
Genbank® Accession No. U83661 Human multidrug resistance–associated protein homolog (MRP5) mRNA, partial cds. Sep. 27, 1997.
Genbank® Accession No. 2439974 multidrug resistance–associated protein homolog [*Homo sapiens*] Sep. 26, 1997.
Genbank® Accession No. U83661 Human multidrug resistance–associated protein homolog (MRP5) mRNA, partial cds. Oct. 2, 1997.
Genbank® Accession No. AAB71758 multidrug resistance–associated protein homolog [*Homo sapiens*] Oct. 1, 1997.
Genbank® Accession No. U83661 *Homo sapiens* multidrug resistance protein 5 (MRP5) mRNA, complete cds. Aug. 3, 1999.
Genbank® Accession No. AAB71758 multidrug resistance protein 5 [*Homo sapiens*] Aug. 3, 1999.
Genbank® Accession No. U83661 *Homo sapiens* multidrug resistance protein 5 (MRP5) mRNA, complete cds. Jun. 21, 2000.
Genbank® Accession No. AAB71758 multidrug resistance protein 5 [*Homo sapiens*] Jun. 21, 2000.
Wijnholds et al. Multidrug–resistance protein 5 is a multispecific organic anion transporter able to transport nucleotide analogs. Proc Natl Acad Sci U S A. Jun. 20, 2000;97(13):7476–81.
Kool et al. Analysis of expression of cMOAT (MRP2), MRP3, MRP4, and MRP5, homologues of the multidrug resistance–associated protein gene (MRP1), in human cancer cell lines. Cancer Res Aug. 15, 1997;57(16):3537–47.

* cited by examiner

*Primary Examiner*—Sheela J. Huff
(74) *Attorney, Agent, or Firm*—Lahive & Cockfield, LLP; Elizabeth A. Hanley, Esq.; Debra J. Milasincic, Esq.

(57) ABSTRACT

Compositions and methods are disclosed for improving the effectiveness of a chemotherapeutic regimen to eradicate multidrug-resistant transformed cells from the body of a mammal, preferably from the body of a human. The present disclosure capitalizes on the discovery of a novel multidrug-resistance associated protein (MRP), herein designated MRP-β. The disclosed compositions include MRP-β nucleic acids, including probes and antisense oligonucleotides, MRP-β polypeptides and antibodies, MRP-β expressing host cells, and non-human mammals transgenic or nullizygous for MRP-β. The disclosed methods include methods for attenuating aberrant MRP-β gene expression, protein production and/or protein function. In addition, methods are disclosed for identifying and using a modulator, such as an inhibitor, of MRP-β. Preferably, the modulator is a small molecule.

24 Claims, 13 Drawing Sheets

```
                GGCTCATGCT CGGGAGCGTG GTTGAGCGGC TGGCGCGGTT GTCCTGGAGC AGGGGCGCAG        60
                                                                   M   K   D      3
                GAATTCTGAT GTGAAACTAA CAGTCTGTGA GCCCTGGAAC CTCCACTCAG AGAAG ATG AAG GAT  124
  I   D   I   G   K   E   Y   I   I   P   S   P   G   Y   R   S   V   R   E   R     23
  ATC GAC ATA GGA AAA GAG TAT ATC ATC CCC AGT CCT GGG TAT AGA AGT GTG AGG GAG AGA    184
  T   S   T   S   G   T   H   R   D   R   E   A   A   A   S   K   F   R   R   P     43
  ACC AGC ACT TCT GGG ACG CAC AGA GAC CGT GAA GCA GCA GCC AGT TTC AGG AGA CGA CCG    244
  L   E   C   Q   D   A   L   E   T   A   R   A   E   G   R   L   S   L   D   A     63
  TTG GAA TGC CAA GAT GCC TTG GAA ACA GCA CGA GCC GAG GGC CTC TCT CTT GAT GCC        304
  S   M   H   S   Q   L   R   I   D   E   E   H   P   K   G   K   Y   H   H         83
  TCC ATG CAT TCT CAG CTC AGA ATC CTG GAT GAG GAG CAT CCC AAG GGA AAG TAC CAT CAT    364
  G   L   S   A   L   K   P   I   R   T   T   S   K   H   Q   L   A   R   V   D   N    103
  GGC TTG AGT GCT CTG AAG CCC ATC CGG ACT ACT TCC AAA CAC CAG CTG GCC CGT GTG GAC AAT  424
  A   G   L   F   S   C   M   T   F   S   W   L   S   L   A   R   V   H   E   S   D    123
  GCT GGG CTT TTT TCC TGT TGT ACT ATG ACT TTT TCG TGG CTT TCT CTG GCC CGT GTG CAC GAG TCT GAC  484
  K   K   G   E   L   S   M   E   D   V   W   Q   E   L   N   E   V   G   S   P   D    143
  AAG AAG GGG GAG CTC TCA ATG GAA GAC GTG TGG CAA GAA CTG AAT GAG GTT GGG TCT CCA GAC  544
  V   N   C   R   R   R   L   E   R   V   V   W   F   C   R   T   R   L   I   S   I    163
  GTG AAC TGC AGA AGA AGA CTA GAG AGA GTT GTG TGG TTC TGC CGC ACC AGG CTC ATC TCC ATC  604
  A   A   S   L   R   R   R   V   W   W   H   F   C   R   T   R   L   I   S   I       183
  GCT TCC CTG CGA AGG GTT GTG TGG                                                      664
```

```
G   V   A   P   I   V   V   V   V   I   A   S   V   V   T   F   S   V   H   M   T
GGT GTG GCT CCC ATT GTG GTG GTG GTG ATT GCC AGC GTG GTG ACC TTC TCT GTT CAT ATG ACC   423
                                                                                     1384

L   G   F   D   L   T   T   A   A   Q   A   F   T   V   L   T   V   F   N   S   M
CTG GGC TTC GAT CTG ACA ACA GCA GCA CAG GCA TTC ACA GTG CTC ACA GTC TTC AAT TCC ATG   443
                                                                                     1444

T   F   A   L   K   K   V   T   L   F   S   V   K   S   L   S   E   A   V   A
ACT TTT GCT TTG AAA AAG GTA ACA TTG TTT TCA GTA AAG TCC CTC TCA GAA GCC GTG GCT       463
                                                                                     1504

V   D   R   F   I   K   S   M   F   L   E   M   E   N   A   K   D   K   A   V
GTT GAC AGA TTT ATC AAG AGT ATG TTG CTA GAG ATG GAA AAT GCC AAG GAC AAG GCG TCA       483
                                                                                     1564

A   S   P   H   Q   N   I   K   M   K   T   L   A   K   K   H   S   D   R   N
GCC AGT CCT CAC CAG AAC ATC AAG ATG AAA ACC TTG GCA AAA AAA CAT AGT GAC AGG AAC       503
                                                                                     1624

S   S   I   Q   N   S   P   K   L   T   P   Q   R   T   M   R   E   S   K   S
TCC AGT ATC CAG AAC TCG CCC ACC CCC CAG ACT CGC ATG ACT CGG GAG TCC TCC TCC TCC       523
                                                                                     1684

R   G   K   E   K   V   L   L   R   Q   D   L   S   R   D   K   A   E   A   E
AGG GGC AAG GAG AAG GTG CTC CTG CAG CAG GAC CTG AGT CGG GAC AAG GAG GAG GCG GAA       543
                                                                                     1744

E   Q   G   K   G   H   I   L   L   G   H   P   T   V   L   Q   P   H   S   I   L
GAG CAG GGC AAA GGC CAC ATC CTC CTG GGC CAC CCC ACA GTG CTA CAC CAG CCC CAC AGC CTG   563
                                                                                     1804

G   K   H   G   L   V   K   L   G   V   R   C   G   L   E   S   I   G   D   T
GGC AAA CAC GGT CTG GTT AAA CTG GGA TGC AGT GGA GTG CTA GGA AGT GGA ATC GAT           583
                                                                                     1864

E   I   Q   H   G   I   E   L   Q   L   G   M   T   K   I   S
GAG ATC CAA CAC GGT ATC GAG CAA CTG CAG CTA GGC ATG ACG AAA ATC AGT                   603
                                                                                     1924

L   I   S   A   I   L   Q   M   T   L   G   S   I   A
CTC ATT TCA GCC ATT TTA CAG ATG ACG CTT CTA GGC AGT ATT GCA                            623
                                                                                     1984
```

FIG. 1D

| S   | V   | Y   | G   | V   | Y   | I   | Q   | A   | A   | G   | P   | L   | A   | F   | L   | V   | I   | M   | 863  |
| TCA | GTA | TAT | GGT | GTC | TAC | ATC | CAG | GCT | GCT | GGC | CCC | TTG | GCA | TTC | CTG | GTT | ATT | ATG | 2704 |
| A   | L   | F   | M   | L   | N   | V   | G   | A   | A   | T   | S   | T   | L   | W   | T   | L   | Y   | W   | 883  |
| GCC | CTT | TTC | ATG | CTG | AAT | GTA | GGC | AGC | GCC | TTC | AGC | AGC | TTG | ACC | TGG | TGG | TAC | TGG | 2764 |
| I   | Q   | Q   | G   | S   | N   | G   | H   | T   | T   | V   | T   | R   | G   | S   | N   | S   | L   | D   | 903  |
| ATC | CAA | CAG | GGA | AGC | AAC | GGG | CAT | ACC | ACT | GTG | ACT | CGA | GGA | AGC | AAC | TCG | AGT | GAC | 2824 |
| S   | M   | K   | D   | N   | P   | K   | A   | D   | M   | Q   | Y   | Y   | S   | A   | Y   | L   | S   | A   | 923  |
| AGC | ATG | AAG | GAC | AAT | CCT | AAA | GCC | GAC | ATG | CAG | TAC | TAT | AGC | GCC | TAC | CTC | TCC | GCA | 2884 |
| V   | M   | L   | D   | H   | L   | A   | E   | R   | R   | V   | V   | F   | I   | L   | V   | T   | R   | A   | 943  |
| GTC | ATG | CTG | CAT | CTG | GCT | GAG | AGG | CGA | GTT | GTC | TTT | ATC | CTT | GTG | ACG | CGA | CGA | GCT | 2944 |
| S   | S   | R   | L   | H   | T   | G   | R   | F   | L   | N   | R   | F   | Q   | I   | L   | S   | K   | F   | 963  |
| TCC | CGG | CTG | CAT | ACA | GGG | AGG | TTC | CTC | AAC | AGG | TTT | CAG | ATC | CTT | TCC | AAG | AAG | TTT | 3004 |
| D   | T   | T   | P   | T   | Q   | F   | A   | R   | M   | F   | L   | I   | F   | M   | D   | E   | V   | D   | 983  |
| GAC | ACG | ACC | CCC | ACA | CAG | TTC | GCA | AGG | ATG | TTC | CTC | ATC | TTC | ATG | GAT | GAA | GTT | GAC | 3064 |
| V   | R   | L   | P   | Q   | G   | Q   | A   | G   | W   | F   | L   | V   | I   | V   | P   | L   | F   | C   | 1003 |
| GTG | CGG | CTG | CCG | TTC | TTC | CAG | GCC | GGA | TGG | TTC | TTC | CTG | ATC | GTG | CCC | CTT | TTC | TGT | 3124 |
| V   | G   | M   | I   | H   | A   | G   | R   | V   | L   | I   | R   | L   | E   | L   | K   | R   | L   | D   | 1023 |
| GTG | GGA | ATG | ATC | CAC | GCA | GGA | GGT | GTC | CTG | ATT | CGG | CTG | GAG | CTG | AAG | CGT | CTG | GAC | 3184 |
| L   | F   | S   | M   | F   | H   | P   | L   | V   | S   | H   | I   | T   | G   | L   | Q   | L   | A   | T   | 1043 |
| CTC | TTT | TCA | ATG | TTT | CAC | CCT | CTG | GTC | TCC | CAC | ATC | ACG | GGC | CTG | CAG | CTG | GCC | ACC | 3244 |
| N   | I   | T   | Q   | S   | P   | F   | L   | S   | H   | I   | T   | S   | S   | G   | L   | A   | T   |     | 1063 |
| AAT | ATC | ACG | CAG | TCA | CCT | TTC | CTC | TCC | CAC | ATC | ACG | TCC | AGC | GGC | CTT | GCC | ACC |     | 3304 |

*FIG. 1E*

| | | | | | | | | | | | | | |
|---|---|---|---|---|---|---|---|---|---|---|---|---|---|
| I ATC | H CAC | A GCC | Y TAC | N AAT | K AAA | G GGG | Q CAG | E GAG | F TTT | L CTG | H CAC | R AGA | Y TAC | Q CAG | E GAG | L CTG | L CTG | D GAT | D GAC | 1083 3364 |
| N AAC | Q CAA | A GCT | P CCT | F TTT | F TTT | L TTG | F TTT | C TGT | T ACG | A ATG | M ATG | R CGG | W TGG | L CTG | A GCT | V GTG | R CGG | L CTG | D GAC | 1103 3424 |
| L CTC | I ATC | I ATC | A GCC | L CTC | L CTC | I ATC | T ACC | T ACC | T ACC | A GCC | L CTG | M ATG | I ATC | V GTT | L CTT | M ATG | H CAC | G GGG | Q CAG | 1123 3484 |
| I ATT | P CCC | P CCA | A GCC | Y TAT | A GCG | G GGT | L CTC | S TCT | I ATC | A GCC | Y TAT | L TTA | V GTC | Q CAG | L TTA | T ACG | G GGG | L CTG | F TTC | 1143 3544 |
| Q CAG | F TTT | T ACG | V GTC | R AGA | L CTG | A GCA | S TCT | E GAG | T ACA | E GAA | A GCA | R CGA | F TTC | T ACC | V GTT | S TCG | V GTG | E GAG | Q CAG | 1163 3604 |
| N AAT | H CAC | Y TAC | I ATT | K AAG | T ACT | L CTG | S TCC | L TTG | E GAG | V GTG | T ACC | A GCC | R AGA | I ATT | K AAG | N AAC | K AAG | A GCT | P CCC | 1183 3664 |
| S TCC | P CCT | D GAC | W TGG | P CCC | Q CAG | E GAG | G GGA | E GAG | K AAA | N AAC | E GAG | A GCA | P CCT | E GAG | M ATG | R AGG | Y TAC | A GCT | R CGA | 1203 3724 |
| E GAA | N AAC | L CTC | P CCT | L CTC | V GTC | L CTA | K AAG | K AAA | S TCA | G GGG | T ACG | I ATC | I ATC | K AAA | P CCT | A GCC | L CTC | F TTC | I ATT | 1223 3784 |
| G GGC | I ATT | V GTG | G GGG | P CCT | L CTC | T ACA | G GGA | G GGC | C TGC | I ATC | K AAG | G GGG | M ATG | I ATC | S AGT | D GAT | G GGC | R CGT | L CTG | 1243 3844 |
| V GTG | E GAG | L TTA | L CTC | V GTG | L CTC | R CGG | T ACA | G GGA | S TCA | K AAG | I ATC | K AAG | R

```
V    R    S    N    L    D    P    F    N    Q    Y    T    E    D    Q    I    W    D    A    L                          1303
GTC AGA TCA AAT TTG GAC CCC TTC AAC CAG TAC ACT GAA GAC CAG ATT TGG GAT GCC CTG                                             4024

E    R    T    H    M    K    E    C    I    A    Q    L    P    L    K    L    E    S    E    V                          1323
GAG AGG ACA CAC ATG AAA GAA TGT ATT GCT CAG CTA CCT CTG AAA CTT GAA TCT GAA GTG                                             4084

M    E    N    G    D    N    F    S    V    G    E    R    Q    L    I    C    I    A    R    A                          1343
ATG GAG AAT GGG GAT AAC TTC TCA GTG GGG GAA CGG CAG CTC TTG TGC ATA GCT AGA GCC                                             4144

L    L    R    H    C    K    I    L    I    L    D    T    A    M    D    T    E                                          1363
CTG CTC CGC CAC TGT AAG ATT CTG ATT TTA GAT GAA GCC ACA ATG GAC ACA GAG                                                     4204

T    D    L    L    I    Q    E    T    V    T    I    R    E    A    F    A    D    C    M    L    T                     1383
ACA GAC TTA TTG ATT CAA GAG ACC ATC CGA GAA GCA TTT GCA GAC TGT ATG CTG ACC                                                 4264

I    A    H    R    L    H    T    V    L    G    S    D    R    I    M    V    L    A    Q    G                          1403
ATT GCC CAT CGC CTG CAC ACG GTT CTA GGC TCT GAT AGG ATT ATG GTG CTG GCC CAG GGA                                             4324

Q    V    V    E    F    D    T    P    S    V    L    N    K    V    A    V    K    G    R    F    Y                     1423
CAG GTG GTG GAG TTT GAC ACC CCA TCG GTC CTT CTG AAC AAG GTC GCT GTC AAG                     CGA TTC TAT                     4384

A    M    F    A    A    E    N    K    V    A    V    K    G    *                                                        1437
GCC ATG TTT GCT GCT GCA GAG AAC AAG GTC GCT GTC AAG GGC TGA                                                                 4429

CTCCTCCCTGTTGACGAAGTCTCTTTTCTTTAGAGCATTGCCMYKGMMTKCCTGGGGCGGGCCCCTTCATCGCGTCCTC                                             4508

CTACCGAAACCTTGCCTTTCTGATTTATCTTTCGCACAGCAGTTCCGGATTGGCTTGTGTGTTTCACTTTTAGGGAG                                              4587

AGTCATATTTGATTATTGTATTTATTCCATATTCATGTAAACAAAATTAGTTTTTGTTCTTAATTGCACTCTAAAAG                                              4666

GTTCAGGGAACCGTTATTATAATTGTATCAGAGGCCTATAATGAAGCTTTATACGTGTAGCTATATCTATATAATTC                                              4745

TGTACATAGCCTATATTTACACAGTGAAAAATGTAAGCTGTTTATTTTATATTAAAATAAGCACTGTGCTAAAAAAAAAAA                                          4824

AAAAAAAAAAAAGGGGCCCGC                                                                                                       4847
```

*FIG. 1G*

```
              10        20        30        40        50        60
inputs MALRGFCSADGSDPLWDWNVTWNTSNPDFTKCFQNTVLVWPCFYLWACFPFYFLYLSRH 70        80        90       100       110       120
inputs DRGYIQMTPLNKTKTALGFLLWIVCWADLFYSFWERSRGIFLAPVFLVSPTLLGITTLLA 130       140       150       160       170
inputs TFLIQLERRKGVQSSGIMLTFWLVALVCALAILRSKIMTALKE-DAQVDLFRDITFYVYF
                               :  :: . :.    :::: .
                  -------MKDIDIGKEYIIPSPGYRSVRERTST
                              10        20

180       190       200       210       220       230
inputs SLLIQLVLSCFSDRSPLFSETIHDPNPCPES-SASFLSRITFWWITGLIVRG-YRQPLE
       .: .:  . :: :      ::  :: : :: .: ::.::.:: :. :: :.
       SGTHRDREDSKFRRTRPLECQDALETAARAEGLSLDASMHSQLRILDEEHPKGKYHGLS
              30        40        50        60        70        80

240       250       260       270       280       290
inputs G-SDLWSLNKEDTSEQVVPVLV-KNWKKECAKTRKQPVKVVYSSKDP-AQPK-ESSKVDA
        . : ::: :  . :.   ::  ..    :. :: :. ::: . ..  : :  ::. ::
       ALKPIRTTCKHQHPVDNAGLFSCMTFSWLSSLARVAHKKGELSMEDVWSLSKHESSDVNC
              90       100       110       120       130       140
```

FIG. 2A

```
               300       310       320       330       340
inputs N--EEV--EALIVKSPQKEWNPSLFKVLYKTFGPYFLMSFFFKAIHDLMMFSGPQIL-KL
       : :...: :::  :: .. :::: ....  :: ...  :  .. . . ::::  ::
       RRLERLWQEELNEVGPD---AASLRRVVWIFCRTRLLLSIVCLMITQLAGFSGPAFMVKH
              150       160       170       180       190       200

350       360       370       380       390       400
inputs LIKFVNDTKAPDWQGYFYTVL-LFVTACLQTLVLHQYFHICFVSGMRIKTAVIGAVYRKA
       :::: :: :.. ::.  ::: . :: .::  : : :   : . :.  :::: :::::::
       LLEYTQAT-ESNLQYSLLIVLGLLLTEIVRSWSLALTWALNYRTGVRLRGAILTMAFKKI
              210       220       230       240       250       260

410       420       430       440       450       460
inputs LVITNSARKSSTVGEIVNLMSVDAQRFMDLATYINMIWSAPLQVILALYLLWLNLGPSVL
       : :.. . ::  :: :. :.. .:: :  .: ..:  .: :::::: :::::::::::.
       LKLKN--IKEKSLGELINICSNDGQRMFEAAAVGSLLAGGPVVAILGMIYNVIILGPTGF
              270       280       290       300       310       320

470       480       490       500       510       520
inputs AGVAVMVLMVPVNAVMAMKTKTYQVAHMKSKDNRIKLMNEILNGIKVLKLYAWELAFKDK
        ::...:::: :.:: ..:::::.. . ::::..:::.: ::. ::.:::::: :::::
       LGSAVFILFYPAMMFASRLTAYFRRKCVAATDERVQKMNEVLTYIKFIKMYAWVKAFSQS
              330       340       350       360       370       380

530       540       550       560       570       580
inputs VLAIRQEELKVLKKSAYLSAVGTFTWVCTPFLVALCTFAVYVTIDENNILDAQTAFVSLA
       :.:: ::::. :.:..:  ::.: .. :.::.. ::..::::: .  . :: :.:.::.
       VQKIREEERRILEKAGYFQSITVGVAPIVVIASVVTFSVHMTLGFD--LTAAQAFTVVT
              390       400       410       420       430
```

FIG. 2B

```
                        590            600            610           620
inputs   LFNILRFPLNILPMVISSIVQASVSLKRLR-IFL---------------SHEELE------
         .::. ::...::. . . ::....::... :.::             ..  ::
         VFNSMTFALKVTPFSVKSLSEASVAVDRFKSLFMEEVHMIKNKPASPHIKIEMKNATLA
                  440            450            460           470            480            490

630            640            650
inputs   ----PDSIERRP-----------VKDGGTNSITVRN----------ATF----------TWARSD
             ::. ::.           ::                    ::.                ::
         WDSSHSSIQNSPKLTPKMKKDKRASRGKKEKVRQLQRTEHQAVLAEQKGHLLLDSDERPS
             500            510            520            530            540            550 inputs   PP------------------TLNGITFSIPEGALVAVVGQVGCGKSSLLSALLAEMDKVEGH
         ::                  :: ::                   ::          ::: ::
         PEEEEGKHIHLGHLRLQRTLHSIDLEIQEGKLVGICGSVGSGKTSLISAILGQMTLLEGS
                 560            570            580            590            600            610

710            720            730            740            750            760
inputs   VAIKGSVAYVPQQAWIQNDSLRENILFGCQLEEPYYRSVIQACALLPDLEILPSGDRTEI
         :: :  .  ::.:: :: . ::..::.:                 ::  ::.:::.. ::
         IAISGTFAYVAQQAWILNATLRDNILFGKEYDEERYNSVLNSCCLRPDLAILPSSDLTEI
                 620            630            640            650            660            670

770            780            790            800            810            820
inputs   GEKGVNLSGGQKQRVSLARAVYSNADIYLFDDPLSAVDAHVGKHIFENVIGPKGMLKNKT
         ::: . :::.:: :::: :: :::..: ::::::::::::::::::  :::   .:: ::
         GERGANLSGGQRQRISLARALYSDRSIYILDDPLSALDAHVGNHIFNSAI--RKHLKSKT
                 680            690            700            710            720            730
```

*FIG. 2C*

```
         830       840       850       860       870       880
         :::: :: ::::: :  :: ::::: ::  :::::: ::::: ::::: ::
inputs RILVTHSMSYLPQVDVIIVMSGGKISEMGSYQELLARDGAFAEFLRTYASTEQEQDAEEN
       . :: ::   ::::: ::  :::  : ::::: .  ::::::      ::
       VLFVTHQLQYLVDCDEVIFMKEGCITERGTHEELMNLNGDYATIF-----------NN
         740       750       760       770       780

890       900       910       920       930       940
        ::: ::::  :::: ::: ::::: :::::::::    :   :::   :::::
inputs GVTGVSGPGKEAKQMENGMLVTDSAGKQLQRQLSSSSSYSGDISRHHNSTAELQKAEAKK
                :  :::  ::          :: :   :::::    :       ::::  :
       LLLGETPPVEINSKKE------TSGSQKKSQDKGPKT--GSIKK------EKA-VKP
            790           800          810                    820

950       960       970       980       990      1000
       :::  : ::::  :::::::: :  :: :: ::   ::::::: :::  :::::
inputs EETWKLMEADKAQTGQVKLSVYWDYMKAIGLFISFLSIF-LFMCNHVSALASNYWLSLWT
       ::    ::  ::   ::::::  :::::  :::::  ::::: :::::::::::
       EEGQLVQLEEKGQ-GSVPWSVYGVYIQAAGGPLAFLVIMALFMLNVGSTAFSTWWLSYWI
         830       840       850       860       870       880

1010      1020      1030      1040
       ::  :::::   ::::::::::::::::  ::::      ::
inputs DDPIVNGTQ---EHTKVRLSVYGALGISQGIAVFGYSMAV----SIGGIL-------AS
       :::::::::: : ::::::::::::::::::::::::::  ::::::::::::::
       KQGSGNTTVTRGNETSVSDSMKDNPHMQYYASIYALSMAVMLILKAIRGVVFVKGTLRAS
         890       900       910       920       930       940

1050      1060      1070      1080      1090      1100
       :: :: :::  :::::::::::::::: :::::::::::::: ::::::::: ::
inputs RCLHVDLLHSILRSPMSFFERTPSGNLVNRFSKELDTVDSMIPEVIKMFMGSLFNVIGAC
       ::  ::::::: :::::: ::: :::::::::::: ::::: :::::: :::::: ::
       SRLHDELFRRILRSPMKFFDTTPTGRILNRFSKDMDEVDVRLPFQAEMFIQNVILVF-FC
         950       960       970       980       990      1000
```

*FIG. 2D*

```
                  1110      1120      1130       1140        1150      1160
inputs   IVILLAT-PIAAIIIPPLGLIYFFVQRFYVASSRQLKRLESVSRSPVYSHFNETLLGVSV
         .   .  ::  .   .       .    . ::.:   . ::: :::  ::  . ::.
         VGMIAGVFPWFLVAVGPLVILFSVLHIVSRVLIRELKRLDNITQSPFLSHITSSIQGLAT
              1010      1020      1030      1040      1050      1060

1170      1180      1190      1200       1210        1220
inputs   IRAFEEQERFIHQSDLKVDENQKAYYPSIVANRWLAVRLECVGNCIVLFAALFAVISRHS
         ::  .:.::: :  ::.  .: : .: ::::: :.::.:  :..::.:  .: . .
         IHAYNKGQEFLHRYQELLDDNQAPFFLFTCAMRWLAVRLDLISIALITTTGLMIVLMHGQ
              1070      1080      1090      1100      1110      1120

1230      1240      1250      1260        1270       1280
inputs   LSAGLVGLSVSYSLQVTTYLNMLVRMSSEMETNIVAVERLKEYSETEK-EAPWQIQETAP
         :   ::: : :::..:.: :    :::  ::   ::  :: ::: :  :  ::
         IPPAYAGLAISYAVQLTGLFQFTVRLASETEARFTSVERINHYIKTLSLEAPARIKNKAP
              1130      1140      1150      1160      1170      1180

1290      1300      1310      1320       1330        1340
inputs   PSSWPQVGRVEFRNYCLRYREDLDFVLRHINVTINGGEKVGIVGRTGAGKSSLTLGLFRI
         : .:::.::::: ..:  ::    .::  . .::  :::::::::::::::.:.::::
         SPDWPQEGEVTFENAEMRYRENLPLVLKKVSFTIKPKEKIGIVGRTGSGKSSLGMALFRL
              1190      1200      1210      1220      1230      1240

1350      1360      1370      1380       1390        1400
inputs   NESAEGEIIIDGINIAKIGLHDLREKITIIPQDPVLFSGSLRMNLDPFSQYSDEEVWTSL
         .  . ::::::::.:  ::   ::  :: :::::::::::: :::::: : ::  ::
         VELSGGCIKIDGVRISDIGLADLRSKLSIIPQEPVLFSGTVRSNLDPFNQYTEDQIWDAL
              1250      1260      1270      1280      1290      1300
```

*FIG. 2E*

```
         1410      1420      1430      1440      1450      1460
inputs ELAHLKDFVSALPDKLDHECAEGGENLSVGQRQLVCLARALLRKTKILVLDEATAAVDLE
       :  ::   ::    ::     ::::::::   ::::::::::  ::::: ::::  ::
       ERTHMKECIAQLPLKLESEVMENGDNFSVGERQLLCIARALLRHCKILILDEATAAMDTE
         1310      1320      1330      1340      1350      1360

1470      1480      1490      1500      1510      1520
inputs TDDLIQSTIRTQFEDCTVLTIAHRLNTIMDYTRVIVLDKGEIQEYGAPSDLL-QQRGLFY
       :: ::: :: :: ::: ::::::::  :::: :::::::::  ::      ::::::::
       TDLLIQETIREAFADCTMLTIAHRLHTVLGSDRIMVLAQGQVVEFDTPSVLLSNDSSRFY
         1370      1380      1390      1400      1410      1420

1530
inputs SM-AKDAGLV----
       :: :: ::
       AMFAAAENKVAVKG
         1430
```

FIG. 2F

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 4847 base pairs
      (B) TYPE: nucleic acid
      (C) STRANDEDNESS: single
      (D) TOPOLOGY: linear -continued

```
    (ix) FEATURE:
         (A) NAME/KEY: CDS
         (B) LOCATION: 116..4426

(xi) SEQUENCE DESCRIPTION: SEQ ID NO: 1:

GGCTCATGCT CGGGAGCGTG GTTGAGCGGC TGGCGCGGTT GTCCTGGAGC AGGGGCGCAG      60

GAATTCTGAT GTGAAACTAA CAGTCTGTGA GCCCTGGAAC CTCCACTCAG AGAAG ATG     118
                                                              Met
                                                                1

AAG GAT ATC GAC ATA GGA AAA GAG TAT ATC ATC CCC AGT CCT GGG TAT     166
Lys Asp Ile Asp Ile Gly Lys Glu Tyr Ile Ile Pro Ser Pro Gly Tyr
          5                  10                  15

AGA AGT GTG AGG GAG AGA ACC AGC ACT TCT GGG ACG CAC AGA GAC CGT     214
Arg Ser Val Arg Glu Arg Thr Ser Thr Ser Gly Thr His Arg Asp Arg
         20                  25                  30

GAA GAT TCC AAG TTC AGG AGA ACT CGA CCG TTG GAA TGC CAA GAT GCC     262
Glu Asp Ser Lys Phe Arg Arg Thr Arg Pro Leu Glu Cys Gln Asp Ala
     35                  40                  45

TTG GAA ACA GCA GCC CGA GCC GAG GGC CTC TCT CTT GAT GCC TCC ATG     310
Leu Glu Thr Ala Ala Arg Ala Glu Gly Leu Ser Leu Asp Ala Ser Met
 50                  55                  60                  65

CAT TCT CAG CTC AGA ATC CTG GAT GAG GAG CAT CCC AAG GGA AAG TAC     358
His Ser Gln Leu Arg Ile Leu Asp Glu Glu His Pro Lys Gly Lys Tyr
                 70                  75                  80

CAT CAT GGC TTG AGT GCT CTG AAG CCC ATC CGG ACT ACT TGC AAA CAC     406
His His Gly Leu Ser Ala Leu Lys Pro Ile Arg Thr Thr Cys Lys His
             85                  90                  95

CAG CAC CCA GTG GAC AAT GCT GGG CTT TTT TCC TGT ATG ACT TTT TCG     454
Gln His Pro Val Asp Asn Ala Gly Leu Phe Ser Cys Met Thr Phe Ser
        100                 105                 110

TGG CTT TCT TCT CTG GCC CGT GTG GCC CAC AAG AAG GGG GAG CTC TCA     502
Trp Leu Ser Ser Leu Ala Arg Val Ala His Lys Lys Gly Glu Leu Ser
    115                 120                 125

ATG GAA GAC GTG TGG TCT CTG TCC AAG CAC GAG TCT TCT GAC GTG AAC     550
Met Glu Asp Val Trp Ser Leu Ser Lys His Glu Ser Ser Asp Val Asn
130                 135                 140                 145

TGC AGA AGA CTA GAG AGA CTG TGG CAA GAA GAG CTG AAT GAA GTT GGG     598
Cys Arg Arg Leu Glu Arg Leu Trp Gln Glu Glu Leu Asn Glu Val Gly
                150                 155                 160

CCA GAC GCT GCT TCC CTG CGA AGG GTT GTG TGG ATC TTC TGC CGC ACC     646
Pro Asp Ala Ala Ser Leu Arg Arg Val Val Trp Ile Phe Cys Arg Thr
            165                 170                 175

AGG CTC ATC CTG TCC ATC GTG TGC CTG ATG ATC ACG CAG CTG GCT GGC     694
Arg Leu Ile Leu Ser Ile Val Cys Leu Met Ile Thr Gln Leu Ala Gly
        180                 185                 190

TTC AGT GGA CCA GCC TTC ATG GTG AAA CAC CTC TTG GAG TAT ACC CAG     742
Phe Ser Gly Pro Ala Phe Met Val Lys His Leu Leu Glu Tyr Thr Gln
    195                 200                 205

GCA ACA GAG TCT AAC CTG CAG TAC AGC TTG TTG TTA GTG CTG GGC CTC     790
Ala Thr Glu Ser Asn Leu Gln Tyr Ser Leu Leu Leu Val Leu Gly Leu
210                 215                 220                 225

CTC CTG ACG GAA ATC GTG CGG TCT TGG TCG CTT GCA CTG ACT TGG GCA     838
Leu Leu Thr Glu Ile Val Arg Ser Trp Ser Leu Ala Leu Thr Trp Ala
                230                 235                 240

TTG AAT TAC CGA ACC GGT GTC CGC TTG CGG GGG GCC ATC CTA ACC ATG     886
Leu Asn Tyr Arg Thr Gly Val Arg Leu Arg Gly Ala Ile Leu Thr Met
            245                 250                 255

GCA TTT AAG AAG ATC CTT AAG TTA AAG AAC ATT AAA GAG AAA TCC CTG     934
Ala Phe Lys Lys Ile Leu Lys Leu Lys Asn Ile Lys Glu Lys Ser Leu
        260                 265                 270
```

```
GGT GAG CTC ATC AAC ATT TGC TCC AAC GAT GGG CAG AGA ATG TTT GAG      982
Gly Glu Leu Ile Asn Ile Cys Ser Asn Asp Gly Gln Arg Met Phe Glu
    275                 280                 285

GCA GCA GCC GTT GGC AGC CTG CTG GCT GGA GGA CCC GTT GTT GCC ATC     1030
Ala Ala Ala Val Gly Ser Leu Leu Ala Gly Gly Pro Val Val Ala Ile
290                 295                 300                 305

TTA GGC ATG ATT TAT AAT GTA ATT ATT CTG GGA CCA ACA GGC TTC CTG     1078
Leu Gly Met Ile Tyr Asn Val Ile Ile Leu Gly Pro Thr Gly Phe Leu
                310                 315                 320

GGA TCA GCT GTT TTT ATC CTC TTT TAC CCA GCA ATG ATG TTT GCA TCA     1126
Gly Ser Ala Val Phe Ile Leu Phe Tyr Pro Ala Met Met Phe Ala Ser
            325                 330                 335

CGG CTC ACA GCA TAT TTC AGG AGA AAA TGC GTG GCC GCC ACG GAT GAA     1174
Arg Leu Thr Ala Tyr Phe Arg Arg Lys Cys Val Ala Ala Thr Asp Glu
        340                 345                 350

CGT GTC CAG AAG ATG AAT GAA GTT CTT ACT TAC ATT AAA TTT ATC AAA     1222
Arg Val Gln Lys Met Asn Glu Val Leu Thr Tyr Ile Lys Phe Ile Lys
    355                 360                 365

ATG TAT GCC TGG GTC AAA GCA TTT TCT CAG AGT GTT CAG AAA ATC CGC     1270
Met Tyr Ala Trp Val Lys Ala Phe Ser Gln Ser Val Gln Lys Ile Arg
370                 375                 380                 385

GAG GAG GAG CGT CGG ATA TTG GAA AAA GCC GGG TAC TTC CAG AGC ATC     1318
Glu Glu Glu Arg Arg Ile Leu Glu Lys Ala Gly Tyr Phe Gln Ser Ile
                390                 395                 400

ACT GTG GGT GTG GCT CCC ATT GTG GTG GTG ATT GCC AGC GTG GTG ACC     1366
Thr Val Gly Val Ala Pro Ile Val Val Val Ile Ala Ser Val Val Thr
            405                 410                 415

TTC TCT GTT CAT ATG ACC CTG GGC TTC GAT CTG ACA GCA GCA CAG GCT     1414
Phe Ser Val His Met Thr Leu Gly Phe Asp Leu Thr Ala Ala Gln Ala
        420                 425                 430

TTC ACA GTG GTG ACA GTC TTC AAT TCC ATG ACT TTT GCT TTG AAA GTA     1462
Phe Thr Val Val Thr Val Phe Asn Ser Met Thr Phe Ala Leu Lys Val
    435                 440                 445

ACA CCG TTT TCA GTA AAG TCC CTC TCA GAA GCC TCA GTG GCT GTT GAC     1510
Thr Pro Phe Ser Val Lys Ser Leu Ser Glu Ala Ser Val Ala Val Asp
450                 455                 460                 465

AGA TTT AAG AGT TTG TTT CTA ATG GAA GAG GTT CAC ATG ATA AAG AAC     1558
Arg Phe Lys Ser Leu Phe Leu Met Glu Glu Val His Met Ile Lys Asn
                470                 475                 480

AAA CCA GCC AGT CCT CAC ATC AAG ATA GAG ATG AAA AAT GCC ACC TTG     1606
Lys Pro Ala Ser Pro His Ile Lys Ile Glu Met Lys Asn Ala Thr Leu
            485                 490                 495

GCA TGG GAC TCC TCC CAC TCC AGT ATC CAG AAC TCG CCC AAG CTG ACC     1654
Ala Trp Asp Ser Ser His Ser Ser Ile Gln Asn Ser Pro Lys Leu Thr
        500                 505                 510

CCC AAA ATG AAA AAA GAC AAG AGG GCT TCC AGG GGC AAG AAA GAG AAG     1702
Pro Lys Met Lys Lys Asp Lys Arg Ala Ser Arg Gly Lys Lys Glu Lys
    515                 520                 525

GTG AGG CAG CTG CAG CGC ACT GAG CAT CAG GCG GTG CTG GCA GAG CAG     1750
Val Arg Gln Leu Gln Arg Thr Glu His Gln Ala Val Leu Ala Glu Gln
530                 535                 540                 545

AAA GGC CAC CTC CTC CTG GAC AGT GAC GAG CGG CCC AGT CCC GAA GAG     1798
Lys Gly His Leu Leu Leu Asp Ser Asp Glu Arg Pro Ser Pro Glu Glu
                550                 555                 560

GAA GAA GGC AAG CAC ATC CAC CTG GGC CAC CTG CGC TTA CAG AGG ACA     1846
Glu Glu Gly Lys His Ile His Leu Gly His Leu Arg Leu Gln Arg Thr
            565                 570                 575

CTG CAC AGC ATC GAT CTG GAG ATC CAA GAG GGT AAA CTG GTT GGA ATC     1894
Leu His Ser Ile Asp Leu Glu Ile Gln Glu Gly Lys Leu Val Gly Ile
        580                 585                 590
```

-continued

| | |
|---|---|
| TGC GGC AGT GTG GGA AGT GGA AAA ACC TCT CTC ATT TCA GCC ATT TTA<br>Cys Gly Ser Val Gly Ser Gly Lys Thr Ser Leu Ile Ser Ala Ile Leu<br>595                            600                          605 | 1942 |
| GGC CAG ATG ACG CTT CTA GAG GGC AGC ATT GCA ATC AGT GGA ACC TTC<br>Gly Gln Met Thr Leu Leu Glu Gly Ser Ile Ala Ile Ser Gly Thr Phe<br>610                         615                          620                    625 | 1990 |
| GCT TAT GTG GCC CAG CAG GCC TGG ATC CTC AAT GCT ACT CTG AGA GAC<br>Ala Tyr Val Ala Gln Gln Ala Trp Ile Leu Asn Ala Thr Leu Arg Asp<br>                            630                          635                    640 | 2038 |
| AAC ATC CTG TTT GGG AAG GAA TAT GAT GAA GAA AGA TAC AAC TCT GTG<br>Asn Ile Leu Phe Gly Lys Glu Tyr Asp Glu Glu Arg Tyr Asn Ser Val<br>                        645                        650                    655 | 2086 |
| CTG AAC AGC TGC TGC CTG AGG CCT GAC CTG GCC ATT CTT CCC AGC AGC<br>Leu Asn Ser Cys Cys Leu Arg Pro Asp Leu Ala Ile Leu Pro Ser Ser<br>660                            665                          670 | 2134 |
| GAC CTG ACG GAG ATT GGA GAG CGA GGA GCC AAC CTG AGC GGT GGG CAG<br>Asp Leu Thr Glu Ile Gly Glu Arg Gly Ala Asn Leu Ser Gly Gly Gln<br>           675                        680                        685 | 2182 |
| CGC CAG AGG ATC AGC CTT GCC CGG GCC TTG TAT AGT GAC AGG AGC ATC<br>Arg Gln Arg Ile Ser Leu Ala Arg Ala Leu Tyr Ser Asp Arg Ser Ile<br>690                            695                        700                    705 | 2230 |
| TAC ATC CTG GAC GAC CCC CTC AGT GCC TTA GAT GCC CAT GTG GGC AAC<br>Tyr Ile Leu Asp Asp Pro Leu Ser Ala Leu Asp Ala His Val Gly Asn<br>                            710                          715                    720 | 2278 |
| CAC ATC TTC AAT AGT GCT ATC CGG AAA CAT CTC AAG TCC AAG ACA GTT<br>His Ile Phe Asn Ser Ala Ile Arg Lys His Leu Lys Ser Lys Thr Val<br>                        725                        730                    735 | 2326 |
| CTG TTT GTT ACC CAC CAG TTA CAG TAC CTG GTT GAC TGT GAT GAA GTG<br>Leu Phe Val Thr His Gln Leu Gln Tyr Leu Val Asp Cys Asp Glu Val<br>                            740                          745                    750 | 2374 |
| ATC TTC ATG AAA GAG GGC TGT ATT ACG GAA AGA GGC ACC CAT GAG GAA<br>Ile Phe Met Lys Glu Gly Cys Ile Thr Glu Arg Gly Thr His Glu Glu<br>755                            760                          765 | 2422 |
| CTG ATG AAT TTA AAT GGT GAC TAT GCT ACC ATT TTT AAT AAC CTG TTG<br>Leu Met Asn Leu Asn Gly Asp Tyr Ala Thr Ile Phe Asn Asn Leu Leu<br>770                            775                        780                    785 | 2470 |
| CTG GGA GAG ACA CCG CCA GTT GAG ATC AAT TCA AAA AAG GAA ACC AGT<br>Leu Gly Glu Thr Pro Pro Val Glu Ile Asn Ser Lys Lys Glu Thr Ser<br>                            790                          795                    800 | 2518 |
| GGT TCA CAG AAG AAG TCA CAA GAC AAG GGT CCT AAA ACA GGA TCA ATA<br>Gly Ser Gln Lys Lys Ser Gln Asp Lys Gly Pro Lys Thr Gly Ser Ile<br>                        805                        810                    815 | 2566 |
| AAG AAG GAA AAA GCA GTA AAG CCA GAG GAA GGG CAG CTT GTG CAG CTG<br>Lys Lys Glu Lys Ala Val Lys Pro Glu Glu Gly Gln Leu Val Gln Leu<br>820                            825                        830 | 2614 |
| GAA GAG AAA GGG CAG GGT TCA GTG CCC TGG TCA GTA TAT GGT GTC TAC<br>Glu Glu Lys Gly Gln Gly Ser Val Pro Trp Ser Val Tyr Gly Val Tyr<br>835                            840                        845 | 2662 |
| ATC CAG GCT GCT GGG GGC CCC TTG GCA TTC CTG GTT ATT ATG GCC CTT<br>Ile Gln Ala Ala Gly Gly Pro Leu Ala Phe Leu Val Ile Met Ala Leu<br>850                            855                        860                    865 | 2710 |
| TTC ATG CTG AAT GTA GGC AGC ACC GCC TTC AGC ACC TGG TGG TTG AGT<br>Phe Met Leu Asn Val Gly Ser Thr Ala Phe Ser Thr Trp Trp Leu Ser<br>                        870                        875                    880 | 2758 |
| TAC TGG ATC AAG CAA GGA AGC GGG AAC ACC ACT GTG ACT CGA GGG AAC<br>Tyr Trp Ile Lys Gln Gly Ser Gly Asn Thr Thr Val Thr Arg Gly Asn<br>                        885                        890                    895 | 2806 |
| GAG ACC TCG GTG AGT GAC AGC ATG AAG GAC AAT CCT CAT ATG CAG TAC<br>Glu Thr Ser Val Ser Asp Ser Met Lys Asp Asn Pro His Met Gln Tyr<br>900                            905                        910 | 2854 |

| | |
|---|---|
| TAT GCC AGC ATC TAC GCC CTC TCC ATG GCA GTC ATG CTG ATC CTG AAA<br>Tyr Ala Ser Ile Tyr Ala Leu Ser Met Ala Val Met Leu Ile Leu Lys<br>    915                    920                    925 | 2902 |
| GCC ATT CGA GGA GTT GTC TTT GTC AAG GGC ACG CTG CGA GCT TCC TCC<br>Ala Ile Arg Gly Val Val Phe Val Lys Gly Thr Leu Arg Ala Ser Ser<br>930                    935                    940                    945 | 2950 |
| CGG CTG CAT GAC GAG CTT TTC CGA AGG ATC CTT CGA AGC CCT ATG AAG<br>Arg Leu His Asp Glu Leu Phe Arg Arg Ile Leu Arg Ser Pro Met Lys<br>                  950                    955                    960 | 2998 |
| TTT TTT GAC ACG ACC CCC ACA GGG AGG ATT CTC AAC AGG TTT TCC AAA<br>Phe Phe Asp Thr Thr Pro Thr Gly Arg Ile Leu Asn Arg Phe Ser Lys<br>                 965                    970                    975 | 3046 |
| GAC ATG GAT GAA GTT GAC GTG CGG CTG CCG TTC CAG GCC GAG ATG TTC<br>Asp Met Asp Glu Val Asp Val Arg Leu Pro Phe Gln Ala Glu Met Phe<br>980                    985                    990 | 3094 |
| ATC CAG AAC GTT ATC CTG GTG TTC TTC TGT GTG GGA ATG ATC GCA GGA<br>Ile Gln Asn Val Ile Leu Val Phe Phe Cys Val Gly Met Ile Ala Gly<br>                  995                  1000                1005 | 3142 |
| GTC TTC CCG TGG TTC CTT GTG GCA GTG GGG CCC CTT GTC ATC CTC TTT<br>Val Phe Pro Trp Phe Leu Val Ala Val Gly Pro Leu Val Ile Leu Phe<br>1010                 1015                  1020                1025 | 3190 |
| TCA GTC CTG CAC ATT GTC TCC AGG GTC CTG ATT CGG GAG CTG AAG CGT<br>Ser Val Leu His Ile Val Ser Arg Val Leu Ile Arg Glu Leu Lys Arg<br>                  1030                1035                1040 | 3238 |
| CTG GAC AAT ATC ACG CAG TCA CCT TTC CTC TCC CAC ATC ACG TCC AGC<br>Leu Asp Asn Ile Thr Gln Ser Pro Phe Leu Ser His Ile Thr Ser Ser<br>1045                 1050                  1055 | 3286 |
| ATA CAG GGC CTT GCC ACC ATC CAC GCC TAC AAT AAA GGG CAG GAG TTT<br>Ile Gln Gly Leu Ala Thr Ile His Ala Tyr Asn Lys Gly Gln Glu Phe<br>                  1060                1065                1070 | 3334 |
| CTG CAC AGA TAC CAG GAG CTG CTG GAT GAC AAC CAA GCT CCT TTT TTT<br>Leu His Arg Tyr Gln Glu Leu Leu Asp Asp Asn Gln Ala Pro Phe Phe<br>1075                 1080                  1085 | 3382 |
| TTG TTT ACG TGT GCG ATG CGG TGG CTG GCT GTG CGG CTG GAC CTC ATC<br>Leu Phe Thr Cys Ala Met Arg Trp Leu Ala Val Arg Leu Asp Leu Ile<br>1090                 1095                  1100                1105 | 3430 |
| AGC ATC GCC CTC ATC ACC ACC ACG GGG CTG ATG ATC GTT CTT ATG CAC<br>Ser Ile Ala Leu Ile Thr Thr Thr Gly Leu Met Ile Val Leu Met His<br>                  1110                1115                1120 | 3478 |
| GGG CAG ATT CCC CCA GCC TAT GCG GGT CTC GCC ATC TCT TAT GCT GTC<br>Gly Gln Ile Pro Pro Ala Tyr Ala Gly Leu Ala Ile Ser Tyr Ala Val<br>                  1125                1130                1135 | 3526 |
| CAG TTA ACG GGG CTG TTC CAG TTT ACG GTC AGA CTG GCA TCT GAG ACA<br>Gln Leu Thr Gly Leu Phe Gln Phe Thr Val Arg Leu Ala Ser Glu Thr<br>1140                 1145                  1150 | 3574 |
| GAA GCT CGA TTC ACC TCG GTG GAG AGG ATC AAT CAC TAC ATT AAG ACT<br>Glu Ala Arg Phe Thr Ser Val Glu Arg Ile Asn His Tyr Ile Lys Thr<br>                  1155                1160                1165 | 3622 |
| CTG TCC TTG GAA GCA CCT GCC AGA ATT AAG AAC AAG GCT CCC TCC CCT<br>Leu Ser Leu Glu Ala Pro Ala Arg Ile Lys Asn Lys Ala Pro Ser Pro<br>1170                 1175                  1180                1185 | 3670 |
| GAC TGG CCC CAG GAG GGA GAG GTG ACC TTT GAG AAC GCA GAG ATG AGG<br>Asp Trp Pro Gln Glu Gly Glu Val Thr Phe Glu Asn Ala Glu Met Arg<br>                  1190                1195                1200 | 3718 |
| TAC CGA GAA AAC CTC CCT CTC GTC CTA AAG AAA GTA TCC TTC ACG ATC<br>Tyr Arg Glu Asn Leu Pro Leu Val Leu Lys Lys Val Ser Phe Thr Ile<br>                  1205                1210                1215 | 3766 |
| AAA CCT AAA GAG AAG ATT GGC ATT GTG GGG CGG ACA GGA TCA GGG AAG<br>Lys Pro Lys Glu Lys Ile Gly Ile Val Gly Arg Thr Gly Ser Gly Lys<br>1220                 1225                  1230 | 3814 |

| | | |
|---|---|---|
| TCC TCG CTG GGG ATG GCC CTC TTC CGT CTG GTG GAG TTA TCT GGA GGC<br>Ser Ser Leu Gly Met Ala Leu Phe Arg Leu Val Glu Leu Ser Gly Gly<br>               1235                             1240                       1245 | | 3862 |
| TGC ATC AAG ATT GAT GGA GTG AGA ATC AGT GAT ATT GGC CTT GCC GAC<br>Cys Ile Lys Ile Asp Gly Val Arg Ile Ser Asp Ile Gly Leu Ala Asp<br>1250                          1255                        1260                        1265 | | 3910 |
| CTC CGA AGC AAA CTC TCT ATC ATT CCT CAA GAG CCG GTG CTG TTC AGT<br>Leu Arg Ser Lys Leu Ser Ile Ile Pro Gln Glu Pro Val Leu Phe Ser<br>               1270                             1275                       1280 | | 3958 |
| GGC ACT GTC AGA TCA AAT TTG GAC CCC TTC AAC CAG TAC ACT GAA GAC<br>Gly Thr Val Arg Ser Asn Leu Asp Pro Phe Asn Gln Tyr Thr Glu Asp<br>               1285                             1290                       1295 | | 4006 |
| CAG ATT TGG GAT GCC CTG GAG AGG ACA CAC ATG AAA GAA TGT ATT GCT<br>Gln Ile Trp Asp Ala Leu Glu Arg Thr His Met Lys Glu Cys Ile Ala<br>               1300                             1305                       1310 | | 4054 |
| CAG CTA CCT CTG AAA CTT GAA TCT GAA GTG ATG GAG AAT GGG GAT AAC<br>Gln Leu Pro Leu Lys Leu Glu Ser Glu Val Met Glu Asn Gly Asp Asn<br>               1315                             1320                       1325 | | 4102 |
| TTC TCA GTG GGG GAA CGG CAG CTC TTG TGC ATA GCT AGA GCC CTG CTC<br>Phe Ser Val Gly Glu Arg Gln Leu Leu Cys Ile Ala Arg Ala Leu Leu<br>1330                        1335                        1340                        1345 | | 4150 |
| CGC CAC TGT AAG ATT CTG ATT TTA GAT GAA GCC ACA GCT GCC ATG GAC<br>Arg His Cys Lys Ile Leu Ile Leu Asp Glu Ala Thr Ala Ala Met Asp<br>               1350                             1355                       1360 | | 4198 |
| ACA GAG ACA GAC TTA TTG ATT CAA GAG ACC ATC CGA GAA GCA TTT GCA<br>Thr Glu Thr Asp Leu Leu Ile Gln Glu Thr Ile Arg Glu Ala Phe Ala<br>               1365                             1370                       1375 | | 4246 |
| GAC TGT ACC ATG CTG ACC ATT GCC CAT CGC CTG CAC ACG GTT CTA GGC<br>Asp Cys Thr Met Leu Thr Ile Ala His Arg Leu His Thr Val Leu Gly<br>               1380                             1385                       1390 | | 4294 |
| TCC GAT AGG ATT ATG GTG CTG GCC CAG GGA CAG GTG GTG GAG TTT GAC<br>Ser Asp Arg Ile Met Val Leu Ala Gln Gly Gln Val Val Glu Phe Asp<br>               1395                             1400                       1405 | | 4342 |
| ACC CCA TCG GTC CTT CTG TCC AAC GAC AGT TCC CGA TTC TAT GCC ATG<br>Thr Pro Ser Val Leu Leu Ser Asn Asp Ser Ser Arg Phe Tyr Ala Met<br>1410                        1415                        1420                        1425 | | 4390 |
| TTT GCT GCT GCA GAG AAC AAG GTC GCT GTC AAG GGC TGACTCCTCC<br>Phe Ala Ala Ala Glu Asn Lys Val Ala Val Lys Gly<br>               1430                             1435 | | 4436 |
| CTGTTGACGA AGTCTCTTTT CTTTAGAGCA TTGCCATTCC CTGCCTGGGG CGGGCCCCTT | | 4496 |
| CATCGCGTCC TCCTACCGAA ACCTTGCCTT TCTCGATTTT ATCTTTCGCA CAGCAGTTCC | | 4556 |
| GGATTGGCTT GTGTGTTTCA CTTTTAGGGA GAGTCATATT TTGATTATTG TATTTATTCC | | 4616 |
| ATATTCATGT AAACAAAATT TAGTTTTTGT TCTTAATTGC ACTCTAAAAG GTTCAGGGAA | | 4676 |
| CCGTTATTAT AATTGTATCA GAGGCCTATA ATGAAGCTTT ATACGTGTAG CTATATCTAT | | 4736 |
| ATATAATTCT GTACATAGCC TATATTTACA GTGAAAATGT AAGCTGTTTA TTTTATATTA | | 4796 |
| AAATAAGCAC TGTGCTAAAA AAAAAAAAAA AAAAAAAAA AGGGCGGCCG C | | 4847 |

(2) INFORMATION FOR SEQ ID NO: 2:

(i) SEQUENCE CHARACTERISTICS:
        (A) LENGTH: 1437 amino acids
        (B) TYPE: amino acid
        (D) TOPOLOGY: linear (ii) MOLECULE TYPE: protein -continued (xi) SEQUENCE DESCRIPTION: SEQ ID NO: 2:

```
Met Lys Asp Ile Asp Ile Gly Lys Glu Tyr Ile Ile Pro Ser Pro Gly
 1               5                  10                  15

Tyr Arg Ser Val Arg Glu Arg Thr Ser Thr Ser Gly Thr His Arg Asp
                20                  25                  30

Arg Glu Asp Ser Lys Phe Arg Arg Thr Arg Pro Leu Glu Cys Gln Asp
            35                  40                  45

Ala Leu Glu Thr Ala Ala Arg Ala Glu Gly Leu Ser Leu Asp Ala Ser
        50                  55                  60

Met His Ser Gln Leu Arg Ile Leu Asp Glu Glu His Pro Lys Gly Lys
65                  70                  75                  80

Tyr His His Gly Leu Ser Ala Leu Lys Pro Ile Arg Thr Thr Cys Lys
                85                  90                  95

His Gln His Pro Val Asp Asn Ala Gly Leu Phe Ser Cys Met Thr Phe
            100                 105                 110

Ser Trp Leu Ser Ser Leu Ala Arg Val Ala His Lys Lys Gly Glu Leu
        115                 120                 125

Ser Met Glu Asp Val Trp Ser Leu Ser Lys His Glu Ser Ser Asp Val
130                 135                 140

Asn Cys Arg Arg Leu Glu Arg Leu Trp Gln Glu Leu Asn Glu Val
145                 150                 155                 160

Gly Pro Asp Ala Ala Ser Leu Arg Arg Val Val Trp Ile Phe Cys Arg
                165                 170                 175

Thr Arg Leu Ile Leu Ser Ile Val Cys Leu Met Ile Thr Gln Leu Ala
            180                 185                 190

Gly Phe Ser Gly Pro Ala Phe Met Val Lys His Leu Leu Glu Tyr Thr
        195                 200                 205

Gln Ala Thr Glu Ser Asn Leu Gln Tyr Ser Leu Leu Val Leu Gly
210                 215                 220

Leu Leu Leu Thr Glu Ile Val Arg Ser Trp Ser Leu Ala Leu Thr Trp
225                 230                 235                 240

Ala Leu Asn Tyr Arg Thr Gly Val Arg Leu Arg Gly Ala Ile Leu Thr
                245                 250                 255

Met Ala Phe Lys Lys Ile Leu Lys Leu Lys Asn Ile Lys Glu Lys Ser
            260                 265                 270

Leu Gly Glu Leu Ile Asn Ile Cys Ser Asn Asp Gly Gln Arg Met Phe
        275                 280                 285

Glu Ala Ala Val Gly Ser Leu Leu Ala Gly Gly Pro Val Val Ala
290                 295                 300

Ile Leu Gly Met Ile Tyr Asn Val Ile Ile Leu Gly Pro Thr Gly Phe
305                 310                 315                 320

Leu Gly Ser Ala Val Phe Ile Leu Phe Tyr Pro Ala Met Met Phe Ala
                325                 330                 335

Ser Arg Leu Thr Ala Tyr Phe Arg Arg Lys Cys Val Ala Ala Thr Asp
            340                 345                 350

Glu Arg Val Gln Lys Met Asn Glu Val Leu Thr Tyr Ile Lys Phe Ile
        355                 360                 365

Lys Met Tyr Ala Trp Val Lys Ala Phe Ser Gln Ser Val Gln Lys Ile
370                 375                 380

Arg Glu Glu Glu Arg Arg Ile Leu Glu Lys Ala Gly Tyr Phe Gln Ser
385                 390                 395                 400

Ile Thr Val Gly Val Ala Pro Ile Val Val Ile Ala Ser Val Val
                405                 410                 415
```

-continued

```
Thr Phe Ser Val His Met Thr Leu Gly Phe Asp Leu Thr Ala Ala Gln
            420                 425                 430

Ala Phe Thr Val Val Thr Val Phe Asn Ser Met Thr Phe Ala Leu Lys
        435                 440                 445

Val Thr Pro Phe Ser Val Lys Ser Leu Ser Glu Ala Ser Val Ala Val
    450                 455                 460

Asp Arg Phe Lys Ser Leu Phe Leu Met Glu Glu Val His Met Ile Lys
465                 470                 475                 480

Asn Lys Pro Ala Ser Pro His Ile Lys Ile Glu Met Lys Asn Ala Thr
                485                 490                 495

Leu Ala Trp Asp Ser Ser His Ser Ser Ile Gln Asn Ser Pro Lys Leu
            500                 505                 510

Thr Pro Lys Met Lys Lys Asp Lys Arg Ala Ser Arg Gly Lys Lys Glu
        515                 520                 525

Lys Val Arg Gln Leu Gln Arg Thr Glu His Gln Ala Val Leu Ala Glu
530                 535                 540

Gln Lys Gly His Leu Leu Leu Asp Ser Asp Glu Arg Pro Ser Pro Glu
545                 550                 555                 560

Glu Glu Glu Gly Lys His Ile His Leu Gly His Leu Arg Leu Gln Arg
                565                 570                 575

Thr Leu His Ser Ile Asp Leu Glu Ile Gln Glu Gly Lys Leu Val Gly
            580                 585                 590

Ile Cys Gly Ser Val Gly Ser Gly Lys Thr Ser Leu Ile Ser Ala Ile
        595                 600                 605

Leu Gly Gln Met Thr Leu Leu Glu Gly Ser Ile Ala Ile Ser Gly Thr
    610                 615                 620

Phe Ala Tyr Val Ala Gln Gln Ala Trp Ile Leu Asn Ala Thr Leu Arg
625                 630                 635                 640

Asp Asn Ile Leu Phe Gly Lys Glu Tyr Asp Glu Glu Arg Tyr Asn Ser
                645                 650                 655

Val Leu Asn Ser Cys Cys Leu Arg Pro Asp Leu Ala Ile Leu Pro Ser
            660                 665                 670

Ser Asp Leu Thr Glu Ile Gly Glu Arg Gly Ala Asn Leu Ser Gly Gly
        675                 680                 685

Gln Arg Gln Arg Ile Ser Leu Ala Arg Ala Leu Tyr Ser Asp Arg Ser
    690                 695                 700

Ile Tyr Ile Leu Asp Asp Pro Leu Ser Ala Leu Asp Ala His Val Gly
705                 710                 715                 720

Asn His Ile Phe Asn Ser Ala Ile Arg Lys His Leu Lys Ser Lys Thr
                725                 730                 735

Val Leu Phe Val Thr His Gln Leu Gln Tyr Leu Val Asp Cys Asp Glu
            740                 745                 750

Val Ile Phe Met Lys Glu Gly Cys Ile Thr Glu Arg Gly Thr His Glu
        755                 760                 765

Glu Leu Met Asn Leu Asn Gly Asp Tyr Ala Thr Ile Phe Asn Asn Leu
    770                 775                 780

Leu Leu Gly Glu Thr Pro Pro Val Glu Ile Asn Ser Lys Lys Glu Thr
785                 790                 795                 800

Ser Gly Ser Gln Lys Lys Ser Gln Asp Lys Gly Pro Lys Thr Gly Ser
                805                 810                 815

Ile Lys Lys Glu Lys Ala Val Lys Pro Glu Glu Gly Gln Leu Val Gln
            820                 825                 830
```

-continued

Leu Glu Glu Lys Gly Gln Gly Ser Val Pro Trp Ser Val Tyr Gly Val
                835                 840                 845

Tyr Ile Gln Ala Ala Gly Gly Pro Leu Ala Phe Leu Val Ile Met Ala
            850                 855                 860

Leu Phe Met Leu Asn Val Gly Ser Thr Ala Phe Ser Thr Trp Trp Leu
865                 870                 875                 880

Ser Tyr Trp Ile Lys Gln Gly Ser Gly Asn Thr Thr Val Thr Arg Gly
                885                 890                 895

Asn Glu Thr Ser Val Ser Asp Ser Met Lys Asp Asn Pro His Met Gln
                900                 905                 910

Tyr Tyr Ala Ser Ile Tyr Ala Leu Ser Met Ala Val Met Leu Ile Leu
                915                 920                 925

Lys Ala Ile Arg Gly Val Val Phe Val Lys Gly Thr Leu Arg Ala Ser
                930                 935                 940

Ser Arg Leu His Asp Glu Leu Phe Arg Arg Ile Leu Arg Ser Pro Met
945                 950                 955                 960

Lys Phe Phe Asp Thr Thr Pro Thr Gly Arg Ile Leu Asn Arg Phe Ser
                965                 970                 975

Lys Asp Met Asp Glu Val Asp Val Arg Leu Pro Phe Gln Ala Glu Met
                980                 985                 990

Phe Ile Gln Asn Val Ile Leu Val Phe Phe Cys Val Gly Met Ile Ala
                995                 1000                1005

Gly Val Phe Pro Trp Phe Leu Val Ala Val Gly Pro Leu Val Ile Leu
            1010                1015                1020

Phe Ser Val Leu His Ile Val Ser Arg Val Leu Ile Arg Glu Leu Lys
1025                1030                1035                1040

Arg Leu Asp Asn Ile Thr Gln Ser Pro Phe Leu Ser His Ile Thr Ser
                1045                1050                1055

Ser Ile Gln Gly Leu Ala Thr Ile His Ala Tyr Asn Lys Gly Gln Glu
                1060                1065                1070

Phe Leu His Arg Tyr Gln Glu Leu Leu Asp Asp Asn Gln Ala Pro Phe
            1075                1080                1085

Phe Leu Phe Thr Cys Ala Met Arg Trp Leu Ala Val Arg Leu Asp Leu
            1090                1095                1100

Ile Ser Ile Ala Leu Ile Thr Thr Gly Leu Met Ile Val Leu Met
1105                1110                1115                1120

His Gly Gln Ile Pro Pro Ala Tyr Ala Gly Leu Ala Ile Ser Tyr Ala
                1125                1130                1135

Val Gln Leu Thr Gly Leu Phe Gln Phe Thr Val Arg Leu Ala Ser Glu
                1140                1145                1150

Thr Glu Ala Arg Phe Thr Ser Val Glu Arg Ile Asn His Tyr Ile Lys
                1155                1160                1165

Thr Leu Ser Leu Glu Ala Pro Ala Arg Ile Lys Asn Lys Ala Pro Ser
            1170                1175                1180

Pro Asp Trp Pro Gln Glu Gly Glu Val Thr Phe Glu Asn Ala Glu Met
1185                1190                1195                1200

Arg Tyr Arg Glu Asn Leu Pro Leu Val Leu Lys Lys Val Ser Phe Thr
                1205                1210                1215

Ile Lys Pro Lys Glu Lys Ile Gly Ile Val Gly Arg Thr Gly Ser Gly
                1220                1225                1230

Lys Ser Ser Leu Gly Met Ala Leu Phe Arg Leu Val Glu Leu Ser Gly
            1235                1240                1245

-continued

```
Gly Cys Ile Lys Ile Asp Gly Val Arg Ile Ser Asp Ile Gly Leu Ala
    1250                1255                1260
Asp Leu Arg Ser Lys Leu Ser Ile Ile Pro Gln Glu Pro Val Leu Phe
1265                1270                1275                1280
Ser Gly Thr Val Arg Ser Asn Leu Asp Pro Phe Asn Gln Tyr Thr Glu
            1285                1290                1295
Asp Gln Ile Trp Asp Ala Leu Glu Arg Thr His Met Lys Glu Cys Ile
        1300                1305                1310
Ala Gln Leu Pro Leu Lys Leu Glu Ser Glu Val Met Glu Asn Gly Asp
            1315                1320                1325
Asn Phe Ser Val Gly Glu Arg Gln Leu Leu Cys Ile Ala Arg Ala Leu
    1330                1335                1340
Leu Arg His Cys Lys Ile Leu Ile Leu Asp Glu Ala Thr Ala Ala Met
1345                1350                1355                1360
Asp Thr Glu Thr Asp Leu Leu Ile Gln Glu Thr Ile Arg Glu Ala Phe
            1365                1370                1375
Ala Asp Cys Thr Met Leu Thr Ile Ala His Arg Leu His Thr Val Leu
        1380                1385                1390
Gly Ser Asp Arg Ile Met Val Leu Ala Gln Gly Gln Val Val Glu Phe
            1395                1400                1405
Asp Thr Pro Ser Val Leu Leu Ser Asn Asp Ser Ser Arg Phe Tyr Ala
        1410                1415                1420
Met Phe Ala Ala Ala Glu Asn Lys Val Ala Val Lys Gly
1425                1430                1435
```

(2) INFORMATION FOR SEQ ID NO: 3:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO: 3:

```
GCGTCCGCCT AGAACGCAGA GATGAGGTAC CGAGAAAACC TCCCTCTCGT CCTAAAGAAA      60

GTATCCTTCA CGATCAAACC TAAAGAGAAG ATTGGCATTG TGGGGCGGAC AGGATCAGGG     120

AAGTCCTCGC TGGGGATGGC CCTCTTCCGT CTGGTGGAGT TATCTGGAGG CTGCATCAAG     180

ATTGATGGAG TGAGAATCAG TGATATTGGC CTTGCCGACC TCCGAAGCAA ACTCTCTATC     240

ATTCCTCAAG AGCCGGTGCT GTTCAGTGGC ACTGTCAGAT CAAATTTGGA CCCTTCAACC     300

AGTACACTGA AGACCAGATT TGGGATGCCC TGGAAAGGAC ACACATGAAA GAATGTATTG     360

CTCCAGCTAC CTCCTGAAAC TTGAATCCTG AATTTGATGG AGAAATGGGG AAATAACTTC     420

TCCAGTTGGG GGAAACGGCA CTCTTTGTTG CCATACCTAN ACC                       463
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 4:

```
TGCTGGTTCT CTCCCTCACA CTTC                                             24
```

-continued (2) INFORMATION FOR SEQ ID NO: 5:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (xi) SEQUENCE DESCRIPTION: SEQ ID NO: 5:

CTCGGCTCGG GCTGCTGTTT CCAA     24

(2) INFORMATION FOR SEQ ID NO: 6:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (xi) SEQUENCE DESCRIPTION: SEQ ID NO: 6:

GGGTGCTGGT GTTTGGAAGT AGTC     24

(2) INFORMATION FOR SEQ ID NO: 7:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (xi) SEQUENCE DESCRIPTION: SEQ ID NO: 7:

GCCAGAGAAG AAAGCCACGA AAAA     24

(2) INFORMATION FOR SEQ ID NO: 8:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (xi) SEQUENCE DESCRIPTION: SEQ ID NO: 8:

AGGCACACGA TGGACAGGAT GAGC     24

MULTIDRUG RESISTANCE-ASSOCIATED POLYPEPTIDE

This patent application is a continuation application of U.S. patent application Ser. No. 09/061,400, filed on Apr. 16, 1998 (U.S. Pat. No. 6,077,936), which in turn is a continuation-in-part of U.S. Ser. No. 08/843,459, filed Apr. 16, 1997 (U.S. Pat. No. 6,162,616), the disclosures of which are incorporated herein by reference.

FIELD OF THE INVENTION

The present invention relates generally to cancer chemotherapy. The invention relates more specifically to compositions and methods for improving the effectiveness of a chemotherapeutic regimen to eradicate multidrug-resistant transformed cells from the body of a mammal, preferably from the body of a human. In this regard, the invention capitalizes on the discovery of a novel multidrug-resistance associated polypeptide (MRP), herein designated MRP-β. The invention further relates to drug discovery, especially to the design of novel chemotherapeutic drugs that are cytotoxic to cells expressing MRP-β.

BACKGROUND OF THE INVENTION

Cancer chemotherapy involves the administration of one or more cytotoxic or cytostatic drugs to a cancer sufferer. The goal of chemotherapy is to eradicate a substantially clonal population (colony) of transformed cells from the body of the individual, or to suppress or to attenuate growth of the colony, which is most commonly referred to as a tumor. Tumors may occur in solid or liquid form, the latter comprising a cell suspension in blood or another body fluid. A secondary goal of chemotherapy is stabilizaon (clinical management) of the afflicted individual's health status. Although the tumor may initially respond to chemotherapy by, e.g., stabilizing or reducing its growth rate, in many instances the initial chemotherapeutic treatment regimen becomes less effective or ceases to impede tumor growth. Conventional treatment regimes endorse the use of additional or substitute chemotherapeutic drugs, including drug combinations, in an effort to regain control over tumor growth. However, it is well known that transformed cells in a tumor may acquire resistance to a broad spectrum of chemotherapeutic drugs, including drugs to which the tumor has not hitherto been exposed during treatment. This acquisition of a multidrug-resistant (or multidrug-resistance) phenotype significantly constrains the chemotherapeutic choices available to the clinician, and significantly worsens prognosis for the afflicted individual. Acquisition of multidrug resistance is particularly problematic in carcinomas originating in secretory epithelia, including lung, gastrointestinal tract, mammary, reproductive tract, endocrine and neuroendocrine epithelia.

Tumor cell transformation is the process by which a cell escapes normal control mechanisms governing the cell's tissue-specific phenotype and differentiation state. Thus, transformation often involves "dedifferentiation," which is defined as an inappropriate return to a less committed or less tissue-specific phenotype. Alternatively, transformation involves incomplete or arrested differentiation of cells normally responsible for replenishing cells lost to normal tissue turnover. Transformed cells of epithelial origin produce tumors that are carcinoma cell colonies (carcinomas). When in a gland-like configuration or derived from secretory tissue, such epithelium-derived tumors are referred to as adenocarcinomas. In contrast, transformed cells of mesenchymal origin produce tumors that are sarcoma cell colonies (sarcomas). Transformed cells of the hematopoietic lineage produce leukemias, lymphomas or lymphosarcomas, each of which often occur as cell suspension tumors. In contrast, the primary tumor growth of a carcinoma or sarcoma usually remains near the site of initial cell transformation. However, secondary foci (metastases) of tumor growth can arise at other sites, which can be far removed from the primary tumor growth site. The presence and/or abundance of metastases indicates the degree to which transformed cells have strayed from their normal tissue-specific phenotype and/or acquired invasive properties.

Phenotypically, cell transformation involves the display of altered or abnormal structural (e.g. antigenic) and functional cellular properties. These altered properties provide the transformed cell with a survival or growth advantage over neighboring, non-transformed cells in its tissue of origin. The advantage may arise from acquisition of autocrine growth regulation, abnormal activation of genes controlling or regulating the cell division cycle, abnormal suppression of genes needed for normal exit from or arrest of the cell division cycle, or other changes affecting cell growth and/or survival. Over time, divisions of the transformed cell produce a colony (tumor) of daughter cells each having the phenotypic advantage gained by the original transformed cell. The imposition of chemotherapy subjects the tumor to selection pressure, in effect encouraging further phenotypic change by which tumor cells may escape the cytotoxic effects of a chemotherapeutic drug. Thus, the structural and functional properties of transformed cells in a tumor can fluctuate over time and over the course of chemotherapeutic treatment.

A significant survival advantage is associated with the acquisition of a multidrug-resistance phenotype, which arises from expression of a cellular gene encoding a protein that removes diverse chemotherapeutic drugs or drug metabolites from the intracellular milieu. Drug export diminishes cytotoxic effect, thereby protecting the transformed cell from otherwise lethal chemotherapeutic drugs or drug concentrations. To date, two genes encoding multidrug-resistance export proteins have been identified in the human genome. The first of these, MDR1, encodes P-glycoprotein, a 170 kDa multispanning transmembrane protein belonging the ATP Binding Cassette (ABC) Transporter protein superfamily. Lautier et al. (1996), 52 *Biochem. Pharmacol* 967–977. Superfamily members are multispanning transmembrane proteins that transport substances into or out of the intracellular environment in an energy-dependent manner. Higgins (1992), 8 *Ann. Rev. Cell Biol.* 67–113, provides a general overview of the properties and natural occurrence of superfamily member proteins. ABC transporters have been identified for a large variety of structurally diverse transported substrates, including sugars, peptides, inorganic ions, amino acids, polysaccharides and proteins. Individual transporter proteins appear to function unidirectionally, i.e., to carry out either export or import of intracellular substances. Thus, P-glycoprotein functions by exporting chemotherapeutic drugs which, although structurally heterogenous, appear to share hydrophobic properties. P-glycoprotein overexpression correlates with the presence of a multidrug-resistance phenotype in diverse tumor cell isolates and tumorigenic cell lines. Significant effort has been invested in the development of agents to block or attenuate P-glycoprotein mediated drug export. Such agents are referred to commonly as "chemosensitizers" or "MDR reversal agents," and are disclosed in Hait et al. (1992), U.S. Pat. No. 5,104,858; Sunkara et al. (1993), U.S. Pat. No.

5,182,293; Sunkara et al. (1993), U.S. Pat. No. 5,190,957; Ramu et al. (1993), U.S. Pat. No. 5,190,946; Powell et al. (1995), U.S. Pat. No. 5,387,685; Piwnica-Worms (1995), U.S. Pat. No. 5,403,574; Sarkadi et al. (1995), PCT Publication WO 95/31474; Sunkara et al. (1996), U.S. Pat. No. 5,523,304; Zelle et al. (1996), U.S. Pat. No. 5,543,423; Engel et al. (1996), U.S. Pat. No. 5,556,856; Powell et al. (1996), U.S. Pat. No. 5,550,149 and Powell et al. (1996), U.S. Pat. No. 5,561,141. However, P-glycoprotein overexpression does not account for all instances of the acquisition of a multidrug-resistance phenotype. Lautier et al. (1996), 52 *Biochem, Pharmacol.* 967–977.

A second multidrug-resistance gene identified to date in the human genome encodes multidrug-resistance associated protein (MRP), a 190 kDa multispanning transmembrane protein also belonging to the ABC Transporter protein superfamily. MRP is described in Deeley et al. (1996), U.S. Pat. No. 5,489,519, the teachings of which are incorporated by reference herein. MRP shares only 15% sequence identity with P-glycoprotein at the amino acid level. In addition, MRP differs from P-glycoprotein in its ability to expel specific types of chemotherapeutic drugs from the intracellular milieu. These differences are thought to arise from differences in the drug expulsion mechanism of the two proteins: MRP appears to act on a glutathione-derivatized drug metabolite, whereas P-glycoprotein appears to act on an underivatized drug. Lautier et al. (1996), 52 *Biochem. Pharmacol.* 967–977. Significantly, agents that block or interfere with P-glycoprotein function appear to have little crossreactivity with MRP. Thus, significant effort is being invested in the development of substances (MDR reversal agents) that block or inhibit MRP function.

Overexpression of either P-glycoprotein or MRP can endow a transformed cell with a multidrug-resistance phenotype; thus, empirical testing is required to determine whether a particular reversal agent will be effective for interfering with a tumor's multidrug resistance phenotype. Currently, it is unclear whether MRP and/or P-glycoprotein expression accounts for all occurrences of the multidrug-resistance phenotype, which arises fairly commonly during the course of chemotherapeutic treatment, irrespective of the tissue specificity of the primary tumor. Moreover, the expression patterns of MRP and P-glycoprotein within a given cell population have been observed to fluctuate over time. Thus, exposure to a reversal agent that interferes with P-glycoprotein function may impose selection pressure favoring the expression of MRP. Such pressure would result in continued viability of cells having a multidrug resistance phenotype. Lautier et al. (1996), 52 *Biochem. Pharmacol* 967–977.

Needs remain for preventing or reversing the acquisition of a multidrug resistance phenotype in transformed cells. Particular needs remain to establish the mechanism(s) by which the multidrug resistance phenotype can be produced, and to provide additional therapies for restoring drug sensitivity to multidrug-resistant transformed cells. Still more particular needs remain to improve the clinical management of multidrug resistant tumors, especially when the multidrug resistance phenotype arises entirely or partially from over-expression of one or more genes other than those encoding P-glycoprotein or MRP.

SUMMARY OF THE INVENTION

The present invention capitalizes on the unexpected discovery of a novel gene encoding a hitherto-unknown multidrug-resistance associated polypeptide (MRP). This novel polypeptide, designated herein as MRP-β, is encoded in the human genome and is expected to be found in the genomes of additional mammals. MRP-β likely is a transmembrane-spanning, energy-dependent transporter or pump, as are other members of the ATP Binding Cassette (ABC) Transporter Protein superfamily to which the known proteins MRP and P-glycoprotein belong. It is likely that MRP-β is disposed in the plasma membrane of a mammalian cell, and functions by ejecting intracellular substances, such as chemotherapeutic drugs. Alternatively, MRP-β may span a vesicular membrane, and function by sequestering intracellular substances. Elevated levels of expression of the novel MRP-β gene, or of bioactivity of the novel MRP-β polypeptide encoded by this gene, accordingly are expected to contribute to the emergence and/or persistence of a multidrug-resistance phenotype in transformed mammalian cells, such as carcinoma cells, including adenocarcinoma cells. Elevated expression or bioactivity of MRP-β similarly is expected to contribute to the occurrence of a multidrug-resistance phenotype in sarcoma cells and in transformed cells of the hematopoietic lineage, including leukemias, lymphomas and lymphosarcomas. MRP-β is likely to account for multidrug-resistant mammalian cell phenotypes that are refractory to treatment with reversal agents that interfere with expression, production and/or function of P-glycoprotein or of MRP.

Accordingly, it is an object of this invention to provide nucleic acids and expression vectors encoding MRP-β or a unique fragment thereof. It is another object to provide nucleic acids, including probes and antisense oligonucleotides, complementary to MRP-β encoding nucleic acids. An additional object is to provide methods and compositions for mitigating aberrant expression of an MRP-β gene, or for mitigating aberrant bioactivity of an MRP-β polypeptide. It is yet another object to provide methods and compositions for characterizing and/or attenuating a multidrug resistance phenotype. It is still another object to provide methods and compositions, including MRP-β expressing host cells, for identifying one or more modulators, preferably inhibitors, of MRP-β. A still further object includes the modulation, preferably the inhibition, of MRP-β and of disease states associated with MRP-β. A yet further object includes the potentiation of chemotherapy to eradicate multidrug resistant transformed cells from the body of an individual, such as a cancer patient. These and other objects, along with advantages and features of the invention disclosed herein, will be apparent from the description, drawings and claims that follow.

In a first aspect, the invention features nucleic acids encoding or complementary to MRP-β or a unique fragment thereof. A preferred embodiment provides nucleic acid, the sequence of which comprises SEQ ID No: 1, an MRP-βcDNA sequence. Another preferred embodiment provided MRP-β cDNA deposited on Apr. 16, 1997, under the terms of the Budapest Treaty with the Culture Collection (ATCC), 10801 University Boulevard Manassas, Va. 20110-2209. The deposited cDNA is herein designated fohd013a05m and is accorded Deposit No. 9409. Another preferred embodiment provides ribonucleic acid (RNA) encoding an MRP-β polypeptide, the amino acid sequence of which comprises SEQ ID No: 2. Messenger RNA (mRNA) encoding MRP-β is approximately 6 kilobases (kb) in length. Other embodiments provide unique fragments (e.g., SEQ ID No: 3) of the MRP-β cDNA, including fragments corresponding to portions of the open-reading frame (ORF), and fragments corresponding to untranslated sequences 3' or 5' to the ORF. These unique fragments can be used to produce or design probes for the analysis of cellular MRP-β expression patterns, e.g., for purposes of diagnosing an abnormality in or contributed to by MRP-β. In addition, the present fragments can be used for the production or design of polymerase chain reaction (PCR) primers or antisense oligonucleotides, including therapeutic oligonucleotides that disrupt cellular MRP-β gene expression, especially abnormal or aberrant expression. It will be understood that the present nucleic acids, especially probes and oligonucleotides, may be detectably labelled and/or may comprise one or more modifications in a nucleotide base, backbone sugar or phosphate, or be linked together by linkages other than phosphodiester bonds.

The invention is further embodied in nucleic acids that hybridize to SEQ ID No: 1 or to the complement thereof. Preferred nucleic acids hybridize to SEQ ID No: 1 or to the complement thereof under stringent conditions. Preferred antisense and/or primer oligonucleotides hybridize to unique fragments of SEQ ID No: 1 or of the complement thereof, e.g., under intracellular conditions. Additional MRP-β variant nucleic acids provided herein comprise nucleotide sequences at least 50%, preferably 60%, 70%, 80%, more preferably 90% and even more preferably 95% identical to SEQ ID No: 1. The present variant nucleic acids comprise nucleotide mutations (substitutions, deletions and/or insertions) distributed in any random or non-random frequency within the SEQ ID No: 1 sequence. The invention further provides degenerate variant nucleic acids that encode the SEQ ID No: 2 polypeptide or a unique fragment thereof. In yet further embodiments, the invention provides nucleic acids encoding variant MRP-β polypeptides, comprising amino acid sequences sharing at least 75% sequence similarity with the SEQ ID No: 2 polypeptide. Preferably, these nucleic acids encode polypeptides sharing at least 80%, 85%, 90% or more preferably 95% amino acid sequence similarity with the SEQ ID No: 2 MRP-β polypeptide. The encoded variant polypeptides comprise amino acid mutations (substitutions, deletions and/or insertions) distributed in any random or non-random frequency within the SEQ ID No: 2 sequence. "Similarity" as used herein refers to the sum of aligned amino acid residues that are identical to the corresponding SEQ ID No: 2 residues and those that are allowed point mutations therefor. Moderate gaps and/or insertions (e.g., less than about 50, preferably less than about 15, more preferably less than about 5 amino acid residues) in the aligned sequence are ignored for similarity calculation purposes. Allowed point mutations are substitutions by amino acid residues that are physically and/or functionally similar to the corresponding aligned SEQ ID No: 2 residues, e.g., that have similar size, shape, hydrophilic or hydrophobic character, charge and chemical properties.

It should be understood that the present invention provides oligonucleotides that hybridize to any of the foregoing variant MRP-β nucleic acids, i.e., to nucleic acids that encode polypeptides comprising amino acid sequences that share at least 75% sequence similarity with the SEQ ID No: 2 polypeptide. More particularly, the invention provides olignucleotides that hybridize to one or more unique fragments of nucleic acids encoding the present MRP-β polypeptides. For therapeutic purposes and/or for PCR investigative or diagnostic purposes, the present oligonucleotides hybridize to a unique fragment comprising 5' untranslated sequence, a transcription initiation site, ORF or polypeptide coding sequence, intron-exon boundary, polyadenylation site or 3' untranslated region of the present MRP-β nucleic acids. Exemplary antisense oligonucleotides are disclosed herein (SEQ ID Nos: 4, 5, 6, 7 and 8).

For antisense-oligonucleotide based therapeutic purposes, one or more of the present antisense MRP-β oligonucleotides (optionally comprising one or more modified moieties as disclosed herein) is formulated together with a pharmaceutically acceptable vehicle to produce an antisense pharmaceutical composition suitable for local or systemic administration to a mammal, or for treatment of mammalian cells or tissue whether in situ or ex vivo. In an alternative embodiment, the present antisense oligonucleotide is encoded by an antisense expression vector comprising a nucleic acid insert complementary to the oligonucleotide sequence. The antisense vector preferably comprises or is packaged with one or more retroviral elements for infection of mammalian cells, and further comprises one or more conventional expression control elements (e.g., a promoter, transcriptional initiation site, termination site, or the like) to direct intracellular production of the antisense oligonucleotide in infected cells. The present vector also can be formulated with a pharmaceutically acceptable vehicle to produce additional antisense pharmaceutical compositions of the present invention. Thus, the antisense vector, when internalized by a cell (e.g., by retroviral infection, pinocytosis or diffusion), directs the intracellular production of an antisense oligonucleotide which, as do any of the therapeutic antisense oligonucleotides disclosed herein, disrupts cellular expression of an MRP-β gene. Disruption of expression is achieved by interfering with MRP-β gene activation or transcription, by destabilization of MRP-β gene transcripts, or by interference with the translation of MRP-β gene transcripts. In this manner, the present invention provides compositions for mitigating aberrant expression of an MRP-β gene, e.g., expression which contributes to the emergence or persistence of a multidrug-resistant phenotype.

In a second aspect, the invention features an MRP-β polypeptide, the amino acid sequence of which comprises SEQ ID No: 2. More generally, the invention provides MRP-β polypeptides, and unique fragments (epitopes) thereof, that are encoded by any of the above-described MRP-β nucleic acids. For example, the invention provides MRP-5 polypeptides, the amino acid sequences of which comprise a sequence sharing at least 75% sequence similarity (as defined herein) with SEQ ID No: 2. Such MRP-β polypeptides include naturally-occurring variants (e.g., polymorphic variants, phylogenetic counterparts of the presently disclosed human MRP-β, and/or naturally-occurring mutant variants, particularly mutants associated with the process of somatic cell transformation or tumorigenesis) and biosynthetic variants produced by routine molecular engineering techniques. Based upon an assessment of its sequence similarity to known proteins, such as MRP, the present novel MRP-D polypeptide is believed to be a novel member of the ABC Transporter Protein superfamily. Thus, it is anticipated that MRP-β polypeptides will be displayed on the surface of cells expressing an MRP-β gene, such as multidrug resistant tumor cells or transfected host cells. Of course, it is also possible that MRP-β will be incorporated into intracellular phospholipid membranes, such as vesicular membranes. Cellular production of MRP-β is expected to contribute to the emergence and/or persistence of a multidrug-resistant phenotype in transformed mammalian cells. The present invention provides various specific MRP-βpolypeptide embodiments, including MRP-β polypeptides immunogenically displayed on intact host cell membranes or cell-free membrane fractions derived from host cells; MRP-β polypeptides incorporated into synthetic or non-cellular phospholipid membranes or micelles, and MRP-β polypeptides and polypeptide fragments isolated in substantially pure form. Any of the foregoing polypeptides, or unique, immunogenic fragments (epitopes) thereof can be used to induce immune responses in human or nonhuman mammals.

Accordingly, in a third aspect, the invention features an antibody that binds selectively to an epitope unique to MRP-β. Preferably, the invention provides an antibody that binds to an MRP-β epitope that is displayed on the surface of MRP-βexpressing cells, such as transformed or host cells. Antigen-binding fragments of the present antibody also are provided herein. Such fragments include truncated forms of the antibody that retain antigen binding properties, e.g., Fab, $Fab_2$, Fab' and Fv fragments thereof. Such fragments are produced conventionally by enzymatic or chemical cleavage of an intact antibody of the present invention. Alternatively, such fragments can be produced through molecular engineering techniques. In certain embodiments, the present antigen binding fragment is incorporated into a fusion polypeptide, such that the fragment is fused to another polypeptide, such as an immunoglobulin framework polypeptide. An exemplary framework is of human origin. Alternatively, the antigen-binding region is fused to a non-immunoglobulin polypeptide, e.g., to a cytotoxin or to a chemoattractant polypeptide. A cytotoxin polypeptide induces or mediates cell death (cytolysis), e.g., by inducing apoptosis or by disrupting cell metabolism, cell membrane integrity, intracellular fluid volume, or the like. Exemplary cytotoxic fusion proteins comprise ricin, diptheria toxin, or another naturally-sourced toxin of plant, animal or microbial origin. A chemoattractant polypeptide is any polypeptide of mammalian origin that induces or stimulates activation and localization of immune effector cells (e.g., natural killer cells, cytotoxic T cells, macrophages and the like) that typically mediate a cellular proinflammatory immune response. Exemplary chemoattractant fusion proteins comprise a chemokine, lymphokine or cytokine polypeptide (e.g., interleukin-2 (IL2), tumor necrosis factor TNF), and the like).

In a fourth aspect, the invention features expression vectors comprising nucleic acid encoding an MRP-β polypeptide comprising an amino acid sequence that shares at least 75% sequence similarity with SEQ ID No: 2. The nucleic acid sequence of an exemplary expression vector thus comprises SEQ ID No: 1. The nucleic acid sequence of another exemplary expression vector comprises the sequence of MRP-βcDNA deposited on even date herewith. Additional exemplary expression vectors comprise nucleic acid encoding variants, whether biosynthetic or naturally-sourced, of the presently disclosed MRP-β polypeptide. Certain embodiments of the present expression vectors encode chimeric polypeptides in which one or more MRP-β amino acid residues are substituted by the corresponding residues of another ABC Transporter Protein superfamily member, such as MRP or P-glycoprotein. Such embodiments are expected to facilitate elucidation of the molecular basis of multidrug resistance phenotypes, and thence to facilitate design or screening of novel inhibitors of multidrug resistance. In addition to nucleic acid encoding the MRP-β polypeptide, the present expression vectors comprise one or more expression control elements (e.g., promoter, transcriptional initiation site, termination site and the like) to direct the production of the encoded MRP-β polypeptide in prokaryotic or, preferably eukaryotic, host cells. Optionally, the present expression vectors further comprise a selectable marker gene. For use with eukaryotic host cells, the present expression vector may still further comprise one or more retroviral components to promote infectivity and uptake by eukaryotic, preferably mammalian, cells.

Accordingly, a fifth aspect of the present invention features a host cell transfected with an above-described expression vector. A preferred host cell displays a vector-encoded MRP-β polypeptide, comprising a sequence sharing at least 75% sequence similarity with SEQ ID No: 2, on the cell surface. A particularly preferred host cell displays a functional and immunologically detectable MRP-β polypeptide. In other embodiments the vector encoded MRP-β polypeptide may reside within the cell, e.g., as a component of a vesicular membrane. Preferred host cells acquire a multidrug resistance phenotype and are able to eject or sequester intracellular substances, including chemotherapeutic drugs and/or metabolites thereof. The present host cells can be of human or non-human origin, and can be naturally-sourced, adapted to primary culture, or immortalized under culture conditions. Cells that are suitable for production of host cells are herein defined as source cells. Exemplary source cells include normal differentiated mammalian cells (e.g., obtained by biopsy), cells in primary culture (e.g., serially passaged benign or malignant transformed cells), and cell lines (e.g., immortalized transformed cells such as HeLa, MCF-7, and the like). Preferably, mammalian source cells are primate cells, most preferably human cells. For screening or other investigative purposes, such as the production of non-human mammals, rodent, ovine, porcine, bovine or other mammalian source cells may be used. In other embodiments, host cells can be produced from prokaryotic or eukaryotic source cells, e.g., unicellular organisms, such as yeast. Any of the foregoing can be used to produce host cells by standard cell transfection or infection techniques. Thus, an MRP-β expression vector can be stably incorporated into a source cell by transfection, pinocytosis, electroporation, microinjection, retroviral infection or the like. Transfected cells then are cultured under conditions favorable to the selective survival of MRP-βexpressing host cells, e.g., in the presence of a drug cytotoxic to source cells but to which expression of MRP-β or a vector-borne selectable marker gene confers a survival advantage for host cells. Host cells so obtained are useful for the production and characterization of MRP-β antibodies, for investigation of the nature and variety of toxic substances subject to MRP-β transport, and for the screening and identification of MRP-β inhibitors as described herein.

In further embodiments, MRP-β host cells can be produced from uncommitted source cells, preferably embryonic stem cells or blastocyst cells, of non-human mammalian origin. An uncommitted cell is one that is competent to differentiate, under appropriate conditions, into differentiated cells of one or more specific mammalian body tissues. In the present embodiment, an MRP-β expression vector is introduced into an uncommitted embryonic source cell and preferably integrates in a site-specific or nonspecific fashion into the cells' genome to produce a host cell competent to differentiate into one or a plurality of differentiated cell types. Alternatively, the present expression vector resides in the host cell as microsatellite DNA. In some embodiments, the present expression vector confers a tissue-specific pattern of MRP-β expression in tissue arising from the differentiation of uncommitted host cells. Uncommitted host cells can, through manipulation by established techniques, be used to produce non-human mammals that are either transgenic or nullizygous for MRP-β. To produce a transgenic mammal of the present invention, an above-described host embryonic stem cell or blastocyst cell is integrated (e.g., by microinjection) into a non-human mammalian blastocyst, which is thereafter implanted into the uterus of a non-human, pseudopregnant mammal, such as a mouse, rat, rabbit, sheep, goat, pig or cow. Following a normal gestation period, this intrauterine implantation procedure yields a non-human founder mammal, the body tissues of which comprise a mosaic of normal cells and host cells, the latter comprising MRP-β nucleic acid of vector origin. Progeny of the present founder mammal are characterized by germline integration of nucleic acid of vector origin. Transgenic progeny express an MRP-β polypeptide, the amino acid sequence of which comprises a sequence sharing at least 75% sequence similarity with SEQ ID No: 2. Optionally, this polypeptide is expressed in a tissue-specific manner. Thus, transgenic progeny constitutively or inducibly express MRP-β in all or a subset of their body tissues. Cells isolated or, optionally immortalized from, such transgenic tissue are expected to facilitate investigations into the discovery and characterization of MRP-β modulators useful for treatment of multidrug-resistant transformed cells arising in any mammalian body tissue. For example, transgenic progeny and/or their cells can be used to confirm whether substances initially identified as modulators in an in vitro screen suppress MRP-β polypeptide production or biological function in vitro. Advantageously, transgenic progeny provide a tissue source that can be matched to a tissue type for which modulators of multidrug resistance are particularly desired, e.g., which has a known propensity for developing multidrug resistance. Such tissue types include, but are not limited to, mammary, respiratory tract, gastrointestinal tract, urogenital tract, hematopoietic and endocrine system tissue.

To produce a nullizygous mammal of the present invention, an above-described uncommitted source cell is transfected (e.g., infected) with a null vector, which comprises a non-expressible variant of the MRP-β encoding nucleic acid disclosed herein. The null vector further comprises sufficient nucleic acid sequence 5' and 3' to the MRP-β ORF to achieve homologous recombination with any endogenous MRP-β gene present in the source cells' genome. As a result of homologous recombination, any endogenous MRP-β gene is nullified, i.e., replaced by the present non-expressible variant. Appropriate non-expressible variants include antisense-oriented MRP-β nucleic acids, nucleic acids comprising premature stop codons in the ORF, nucleic acids comprising a defective promoter, and the like. The present null host cell is integrated into a blastocyst and implanted into a pseudopregnant mannal to produce a null founder mammal. Progeny of this founder are characterized by gemrline integration of nucleic acid derived from the null vector. Thus, in nullizygous progeny, the ability to express a naturally encoded MRP-β homolog is "knocked out" such that, preferably, the progeny are incapable of developing a multidrug resistance phenotype attributable to MRP-β expression. Such nullizygous progeny and/or their cells can be used to assess potential side effects or undesirable consequences of MRP-β modulator (e.g., inhibitor) therapy. Nullizygous progeny and/or their cells also can be used to detect additional genes that contribute to emergence of a multidrug-resistance phenotype, i.e., genes other than MRP-β, MRP and P-glycoprotein. Cells isolated or cultured from nullizygous progeny can be exposed to selection pressure by culturing them in the presence of a chemotherapeutic drug, and monitoring the cultures for emergence of a drug-resistant phenotype. Optionally, the MRP-β nullizygous progeny provided herein can be crossbred with non-human mammals nullizygous for MRP nd/or P-glycoprotein. Such multiply nullizygous progeny should facilitate screening for additional genes that can contribute to the emergence of a multidrug resistance phenotype.

The above-described MRP-β compositions are useful according to teachings herein for assessing the presence of mutations in an MRP-β gene; assessing MRP-β gene expression level, especially for detecting fluctuations in expression; and, for mitigating aberrant expression and/or biological function of an MRP-β polypeptide. Preferably, the present MRP-β compositions are useful to treat a disease state or other deleterious condition contributed to by aberrant MRP-5 gene expression or biological function. Most preferably, the present MRP-β compositions are useful to attenuate and/or to abrogate a multidrug resistant phenotype, e.g., of transformed cells in the body of a cancer sufferer. As a result, the present invention offers means for potentiating chemotherapy to eradicate multidrug-resistant transformed cells from an individual's body.

Thus, in a sixth aspect, the invention features diagnostic methods for detecting abnormalities in an MRP-5 gene. In one embodiment, the invention provides a method of detecting a mutation or other structural abnormality in an MRP-β gene. Mutations, whether of germline or somatic origin, may indicate whether the process of cell transformation (tumorigenesis) has been initiated or is likely to arise in an individual's tissues. Mutations are detected by obtaining cellular tissue from a mammal, preferably a human, suspected of harboring a variant MRP-β gene, and treating the tissue so as to release nucleic acids therefrom. Preferably the cellular tissue is obtained from a body tissue suspected of comprising transformed cells. Thus, the present method provides information relevant to diagnosis of the presence of a tumor. The method may be practiced with any body tissue type which comprises cells, including body fluid cell suspensions (e.g., blood, lymph, cerebrospinal fluid, peritoneal fluid or ascites fluid). Released cellular nucleic acids are combined, under hybridization conditions, with an oligoucleotide of the present invention, e.g., an oligonucleotide complementary to nucleic acid encoding MRP-β. Preferably, the oligonucleotide is complementary to a unique fragment of the full-length MRP-β nucleic acid. Following incubation with the oligonucleotide under suitable hybridization conditions, the released nucleic acids are assayed for formation of a hybrid comprising the oligonucleotide. In a preferred embodiment wherein the oligonucleotide is complementary to SEQ ID No: 1 or a unique fragment thereof, formation of the hybrid confirms that the individual harbors at least one wild-type MRP-β gene allele (comprising SEQ ID No: 1). Failure to form a hybrid under stringency conditions that do not tolerate base pair mismatching confirms that the individual lacks a wild-type allele, i.e., that the individual harbors an aberrant, e.g., mutant, variant of the MRP-β gene.

In another embodiment, the invention provides a method of assessing expression, especially aberrant expression, of a cellular MRP-β gene. As with the preceding embodiment, aberrant expression may indicate the presence, persistence or reappearance of multidrug-resistant tumor cells in an individual's tissue. More generally, aberrant expression may indicate the occurrence of a deleterious or disease-associated phenotype contributed to by MRP-β. MRP-β gene expression is assessed by obtaining a sample of cellular tissue from a mammal (e.g., a human), preferably from a body site implicated in a possible diagnosis of diseased or malignant tissue, and treating the tissue to release RNA therefrom. Cellular RNA is combined with an MRP-βoligonucleotide generally as described above, and the resulting mixture is assayed for the presence of a hybrid comprising the MRP-β oligonucleotide and a cellular MRP-β gene transcript. In preferred embodiments, the presence and/or relative abundance of this hybrid is expected to indicate aberrant expression of a cellular MRP-β gene, and to correlate with the occurrence in situ of transformed cells, especially transformed cells having a multidrug-resistant phenotype.

Preferably, the foregoing embodiments can be practiced using a detectably labeled or otherwise modified MRP-β oligonucleotide, most preferably with an oligonucleotide comprising a peptide-nucleic acid backbone.

In yet another embodiment, the invention provides a diagnostic method using an above-described antibody or fragment thereof to characterize aberrant MRP-βassociated phenotype, e.g., drug-resistant phenotype of a transformed cell. This method involves obtaining cellular tissue from a mammal (e.g., a human) suspected of harboring transformed cells, and contacting the tissue with an above-described antibody under conditions such that, if cells of the obtained tissue display a recognized epitope unique to MRP-β, an antibody-epitope complex forms. Generally, the method is practiced with intact cells. The practitioner may, however, desire to generate a more sensitive assay for total cellular MRP-β content. In these circumstances, the method is practiced with permeabilized or solubilized cells, which can be produced by exposing the cells to heat, mechanical disruption, detergent, hypo- or hyper-osmotic conditions, and like conventional techniques. After a sufficient period of time has elapsed for formation of the antibody-epitope complex, the tissue is assayed for presence of the complex, formation or abnormal elevation of which indicates presence in the tissue of cells abnormally expressing MRP-β. As disclosed herein, such cells are likely transformed cells characterized by a drug-resistance phenotype.

Information obtained from practice of the foregoing diagnostic methods is expected to be useful in prognostication, staging and clinical management of diseases and other deleterious conditions affecting an individual's health status. In preferred embodiments, the foregoing diagnostic methods provide information useful in prognostication, staging and management of malignancies (tumors) that are characterized by expression of MRP-β and thus by a multidrug-resistance phenotype. The information more specifically assists the clinician in designing chemotherapeutic or other treatment regimes to eradicate such malignancies from the body of an afflicted mammal, typically a human. The present methods can be practiced with any samples of any body tissue type, and are desirable for assessing cellular tissue of mammary, respiratory tract, urogenital tract, endocrine system or immune system origin. The present methods are particularly useful to assess breast biopsy, bronchoalveolar lavage, ovarian, uterine or cervical biopsy, prostate or testicular biopsy, pancreatic biopsy, and spleen, bone marrow or lymph node biopsy samples.

Further general aspects of the invention feature therapeutic methods and compositions, including one or more modulators (stimulators or, preferably, inhibitors) of the expressed MRP-β gene and/or protein. Accordingly, the invention provides means for mitigating (detectably decreasing or otherwise affecting) aberrant expression of an MRP-β gene, or aberrant production or biological function of an MRP-β polypeptide. The invention thus provides means for attenuating an undesirable phenotype, such as a disease-associated phenotype, that is contributed to by MRP-β. In preferred embodiments, the invention provides means for attenuating a multidrug-resistance phenotype, particularly a phenotype contributed to by MRP-β. More particularly, a seventh aspect of the invention features methods for mitigating aberrant expression of an MRP-β gene, and/or aberrant alteration or biological function of an MRP-β polypeptide. One embodiment involves the administration of an antisense pharmaceutical composition of the present invention to a mammal suffering from effects of the aberrant phenotype associated with altered expression and/or function of MRP-β. Another embodiment involves the administration of an antibody or fusion polypeptide of the present invention. In either embodiment, the therapeutic agent is administered systemically or locally under conditions sufficient to mitigate or attenuate the aberrant MRP-β associated phenotype. Preferably, the therapeutic agent is administered under conditions sufficient to destroy cells aberrantly producing MRP-β. In this manner, the invention provides means for destroying multidrug-resistant tumor cells in situ in the body of a mammal. In preferred embodiments, either of the foregoing therapeutic agents can be administered as an adjuvant to conventional chemotherapy. That is, either of the foregoing therapeutic agents can be coadministered together with one or more chemotherapeutic drugs. The present antisense or fusion polypeptide therapeutic agent can be administered prior to, concomitant with, or following administration of one or more chemotherapeutic drugs. In such embodiments, the antisense pharmaceutical composition mitigates resistance of MRP-β expressing cells to the cytotoxic effects of the chemotherapeutic drug. That is, the antisense composition attenuates the MRP-β phenotype, which is expected to be characterized by display of an ABC Transporter Protein family member (MRP-β) and by the property of multidrug resistance. This is accomplished by disrupting activation or transcription of the MRP-β gene, or by destabilizing RNA transcripts thereof. Diminished or discontinued expression of MRP-β renders cells more susceptible to the cytotoxic effects of a chemotherapeutic drug that otherwise would be exported by MRP-β. Similarly, a therapeutically administered cytotoxic fusion polypeptide localizes in the vicinity of cells aberrantly displaying MRP-β, producing cytolysis thereof. A chemoattractant fusion polypeptide also localizes to MRP-β displaying cells, stimulating destruction thereof by macrophages, killer T cells or cytotoxic T cells.

An eighth aspect of the invention features methods for identifying a modulator (a stimulator or, preferably, an inhibitor) of MRP-β. The present modulator is useful for treating a disease or deleterious condition that is contributed to by MRP-β. Preferably, the modulator is a small molecule. In general, the present identification method relies on the use of an MRP-β expressing host cell produced as described herein. Prokaryotic or eukaryotic host cells can be used for purposes of identifying an MRP-βmodulator, however in general, eukaryotic host cells are preferred. Yeast or mammalian cells may be used, as desired or as dictated by specific circumstances. Presently, mammalian host cells, particularly human cells are preferred. The MRP-β expressing host cell is contacted with a candidate modulator, and after a sufficient period of time for modulatory effects to be manifested, the cell is assayed to determine whether the candidate indeed affects MRP-β. In one embodiment, the level of cellular MRP-β gene expression is assayed. A detectable decrease (attenuation) or cessation (abrogation) in MRP-β gene expression indicates that the candidate is an inhibitory modulator or inhibitor. Conversely, a detectable increase (augmentation) in MRP-β gene expression indicates that the candidate is a stimulatory modulator or stimulator. Another embodiment involves assay of the amount or rate of production of MRP-β polypeptide displayed by the cell. A detectable decrease or cessation of immunologically recognized MRP-β polypeptide indicates that the candidate is an inhibitory modulator. In a third embodiment, the host cell is contacted with a substrate (e.g., a cytotoxin) exported or sequestered by MRP-β. The candidate inhibitor is contacted with the host cell prior to, concomitantly with, or following exposure to the substrate. The amount of substrate exported or sequestered by the cell is assessed. A detectable decrease in efflux or sequestration of the substrate indicates that the candidate is an inhibitory modulator. Alternatively, in specific embodiments wherein the substrate is cytotoxic, survival of the host cell is assessed. A detectable decrease in survival indicates that the candidate is an inhibitory modulator. Candidate substances appropriate for screening as MRP-β modulators in any of the foregoing embodiments include natural or synthetic metabolites, toxins, antibiotics, elements of a combinatorial chemistry, nucleotide or peptide library, naturally sourced cell secretion products, cell lysates, and the like. Preferred substances for screening, and preferred modulators, are small molecules.

Accordingly, a ninth aspect of the invention features an MRP-β modulator, especially an inhibitory modulator, identified by any of the above-described methods. Preferably, the modulator is a small molecule, e.g., an element of a combinatorial chemistry library or a low molecular weight natural or synthetic product or metabolite. The modulator may be dispersed in a pharmaceutically acceptable vehicle to produce a multidrug-resistance attenuating pharmaceutical composition of the present invention.

A tenth aspect of the invention thus features modulator-based methods of mitigating aberrant MRP-β expression and/or polypeptide production and/or biological function. The present method involves the step of administering an MRP-β modulator, optionally dispersed in a pharmaceutically acceptable vehicle to a mammal suffering from effects of the MRP-β associated aberrancy. Therapeutic modulation (preferably inhibition) of MRP-β is useful for the treatment, including prophylaxis, remediation and palliation, of any disease or deleterious condition that is contributed to by an abnormality affecting the MRP-β gene, its expression, MRP-β polypeptide production or biological function. In a preferred embodiment, the invention provides a method for improving (potentiating) effectiveness of chemotherapy to eradicate aberrant MRP-βexpressing cells, e.g., multidrug resistant transformed cells, from the body of a mammal. This method involves the steps of administering a chemotherapeutic drug to the mammal, and coadministering an MRP-β modulator identified as described herein. Preferably, the modulator is provided in the form of a multidrug-resistance attenuating composition, i.e., dispersed in a pharmaceutically acceptable vehicle. This method is particularly preferred where a chemotherapy adjuvant is desired to eradicate multidrug-resistant tumor cells. Advantageously, the method can be practiced where a fluid (e.g., leukemia, lymphoma, lymphsarcoma or ascites) tumor is present, or where the situs of a primary or metastatic tumor is deemed unsuitable for surgical intervention or especially where a remontant or reemergent tumor is observed following an initial course of chemotherapeutic treatment. The present embodiments are suitable for the treatment of any tumor, especially of mammary, respiratory tract, urogenital tract, endocrine system or immune system origin.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

FIG. 1A-G is a text representation of an MRP-β cDNA sequence and of the polypeptide sequence encoded therein, as set forth in SEQ ID Nos: 1 and 2.

FIG. 2A-F is a text representation comprising aligned amino acid sequences of the known ABC Transporter Protein superfamily member MRP (described in Deeley et al. (1996) U.S. Pat. No. 5,489,519), and of the novel MRP-β disclosed herein. Dashes (-) indicate gaps introduced to maximize alignment of similar sequences; colons (:) indicate the locations of identical aligned amino acid residues.

DETAILED DESCRIPTION OF PREFERRED EMBODIMENTS

Mammalian cells having a "multidrug-resistance" or "multidrug-resistant" phenotype are characterized by the ability to sequester, export or expel a plurality of cytotoxic substances (e.g., chemotherapeutic drugs) from the intracellular milieu. Cells may acquire this phenotype as a result of selection pressure imposed by exposure to a single chemotherapeutic drug (the selection toxin). Alternatively, cells may exhibit the phenotype prior to toxin exposure, since the export of cytotoxic substances may involve a mechanism in common with normal export of cellular secretion products, metabolites, and the like. Multidrug resistance differs from simple acquired resistance to the selection toxin in that the cell acquires competence to export additional cytotoxins (other chemotherapeutic drugs) to which the cell was not previously exposed. For example, Mirski et al. (1987), 47 *Cancer Res.* 2594–2598, describe the isolation of a multidrug-resistant cell population by culturing the H69 cell line, derived from a human small cell lung carcinoma, in the presence of adriamycin (doxorubicin) as a selection toxin. Surviving cells were found to resist the cytotoxic effects of anthracycline analogs (e.g., daunomycin, epirubicin, menogaril and mitoxantrone), acivicin, etoposide, gramicidin D, colchicine and Vinca-derived alkaloids (vincristine and vinblastine) as well as of adriamycin. Similar selection culturing techniques can be applied to generate additional multidrug-resistant cell populations.

The functional property of multidrug-resistance is associated with expression and cell-surface display of one or more ABC Transporter Protein superfamily members with energy-dependent export function (e.g., P-glycoprotein, MRP or MRP-β as disclosed herein). The cell population described in Mirski et al. (1987) was reported in Cole et al. (1992), 258 *Science* 1650–1654 to overexpress MRP (a correction of the reported MRP sequence appears at 260 *Science* 879). Currently, antibodies specifically reactive with P-glycoprotein or MRP, or nucleic acid probes specific for the corresponding expressed nucleic acid sequences, are used to ascertain the molecular basis of multidrug-resistance in a given cell population. Where the cell population in question includes transformed cells in the body of a cancer sufferer, determination of the molecular basis of the observed phenotype can assist the clinician in ascertaining whether treatment with one of the so-called "chemosensitizers" or "MDR reversal agents," the majority of which affect P-glycoprotein, is appropriate. Thus, knowledge of the molecular basis of the observed phenotype provides information relevant to developing or revising a course of disease management. Zaman et al. (1993), 53 *Cancer Res.* 1747–1750, cautions, however, that the induction or overexpression of MRP does not account for all forms of multidrug-resistance phenotype that are not attributable to P-glycoprotein expression. The discovery of MRP-β, reported herein, establishes that additional members of the ABC Transporter Protein family exist in the mammalian (e.g., human) genome and likely contribute to the occurrence of multidrug-resistance in transformed cells.

MRP-β was identified by computer-assisted screening of a nucleic acid sequence database corresponding to a human endothelial cell cDNA library. The library comprises cDNAs derived from RNA transcripts of genes expressed by differentiated endothelial cells cultured from microvascular tissue of mammary origin. The library was constructed, and nucleic acid components thereof were sequenced, by conventional techniques as set forth in *Current Protocols in Molecular Cloning*, Ausubel et al., eds. (1989), Greene Publishing and Wiley Interscience, New York, N.Y. The known sequence of MRP was used to query the database using the TBLAST N algorithm disclosed in Altschul et al. (1990), 215 *J. Mol. Biol.* 403–410. The query sequence is disclosed in Cole et al. (1992), 258 *Science* 1650–1654 and 260 *Science* 879. See also SEQ ID No: 1 of Deeley et al. (1996), U.S. Pat. No. 5,489,519, the disclosure of which is incorporated by reference herein. The starting search parameters for TBLAST N were as follows: score=200; word length=12.

The foregoing analysis identified a novel nucleic acid sequence with detectable similarity to the query sequence. The novel sequence, disclosed herein as SEQ. ID No: 3, corresponds to a unique fragment of a hitherto unknown multidrug-resistance associated polypeptide, herein designated MRP-β. As defined herein, a "unique fragment" of a protein or nucleic acid is a peptide or oligonucleotide of sufficient length to have a sequence unique to a particular gene or polypeptide, i.e., a sequence not shared by related or unrelated genes or polypeptides. Thus, for example, a unique nucleic acid fragment typically will have at least 16 nucleotide residues, and a unique polypeptide fragment typically will have at least 6 amino acid residues. Preferably, to ensure substantially unique occurrence in a typical higher eukaryotic genome, a unique nucleic acid fragment should have at least 20 nucleotide residues, and a unique polypeptide fragment should have at least 8 amino acid residues. Unique polypeptide fragments are referred to herein as epitopes. The SEQ ID No: 3 unique fragment of MRP-β nucleic acid is 465 nucleotide residues in length and has a sequence approximately 62% identical to that of the corresponding aligned fragment of the MRP gene. In contrast, SEQ ID No: 3 lacks detectable similarity to the product of the MDR1 gene, P-glycoprotein.

A nucleic acid probe was prepared using the SEQ ID No: 3 sequence, as described in EXAMPLE 1 herein, and used for hybridization screening of an appropriate expression (cDNA) library. The screen yielded an MRP-β cDNA having the sequence set forth as nucleotides 674847 of SEQ ID No: 1 herein. This cloned cDNA has been designated fohd013a05m and has been deposited (Apr. 16, 1997) in the American Type Culture Collection under the terms of the Budapest Treaty. The sequence of fohd013a05m accordingly is incorporated herein by reference. The original SEQ ID No: 3 fragment corresponds generally to nucleotides 3701 to 4144 of the cloned SEQ ID No: 1 cDNA. The full-length MRP-β cDNA extends a short distance upstream (5') of the fohd013a05m MRP-β insert. The MRP-β transcript produced in human cells and/or tissue is approximately 6 kb, as visualized in the Northern blot studies described in EXAMPLES 2 and 3. A cDNA comprising 66 nucleotides upstream (5') of the fohd013a05m MRP-β insert was isolated as described in EXAMPLE 1. The cDNA sequence presented in SEQ ID No: 1 comprises the sequence of the fohd013a05m MRP-β insert and the 66 upstream nucleotides. The native 5' end of the cellular MRP-β transcript can also be elucidated readily using a 5'-RACE protocol known in the art, for example as described in Siebert et al. (1995), 23 *Nucl. Acids Res* 1087–1088, and in the Clonetech, Inc. *User Manual for Marathon-Ready cDNA* (1996), the teachings of which are incorporated herein by reference.

The present invention encompasses all MRP-β nucleic acids that can be isolated or constructed by conventional molecular engineering techniques, using the information made available as a result of the present disclosure. Thus, for example, the invention encompasses nucleic acids comprising sequences complementary to all or a unique fragment of the SEQ ID No: 1 cDNA. The sequence of a "complementary" nucleic acid strand is composed of the Watson-Crick base pair partners of the nucleotide residues in a specified nucleic acid, i.e., a guanidine (G) residue corresponding to each cytosine (C) residue in the specified nucleic acid, and an adenine (A) residue corresponding to each thymidine (T) or uracil (U) residue therein. Thus, the invention encompasses RNA having a sequence complementary to SEQ ID No: 1. The present RNA can be obtained as a cell-free lysate or extract (e.g., as described in EXAMPLE 2), or can be isolated in substantially pure form using techniques described in *Current Protocols in Molecular Cloning*, Ausubel et al. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y. The invention further encompasses a nucleic acid probe or primer having a nucleotide sequence complementary to a unique fragment of the MRP-β gene described herein. The probe optionally further comprises a detectable moiety, or creates a detectable complex, when hybridized to the target (MRP-β) sequence. Non-limiting examples of appropriate detectable moieties including fluorophores (e.g., fluorescein, rhodamine, Texas Red and the like), radionucleotides (e.g., $^3$H, $^{14}$C, $^{32}$P and the like), and binding-pair partners (e.g., biotin, avidin or streptavidin). The probe or primer need not be strictly complementary to the target sequence: it is only necessary that a sufficient number of probe nucleotides be capable of forming base pairs with target nucleotides to produce a stable, double-stranded nucleic acid complex under hybridization conditions.

Hybridization is the noncovalent, antiparallel bonding of complementary nucleic acid strands, in which Watson-Crick base pairing is established. To ensure specificity, hybridization should be carried out under stringent conditions, defined herein as conditions of time, temperature, probe length, probe and/or target concentration, osmotic strength, pH, detergent, carrier nucleic acid, etc. that permit no more than an occasional base-pairing mismatch within a probe/target duplex. Highly stringent conditions exclude all but about one base pair mismatch per kb of target sequence. Exemplary highly stringent conditions involve hybridization to membrane immobilized target nucleic acid at a temperature of 65° C. in the presence of 0.5 m NaHPO$_4$, 7% SDS, 1 mM EDTA, followed by washing at 68° C. in the presence of 0.1×SSC, 0.1% SDS. *Current Protocols in Molecular Biology* (1989), Ausubel et al., eds., Greene Publishing and Wiley Interscience, New York, N.Y. In circumstances where relatively infrequent mismatches, e.g., up to about ten mismatches per kb of target, can be tolerated, moderately stringent conditions may be used. For moderate stringency, probe/target hybrids formed under the above conditions are washed at 42° C. in the presence of 0.2×SSC, 0.1% SDS. The invention encompasses all nucleic acids that hybridize to nucleic acid, the sequence of which comprises SEQ ID No: 1 or a unique fragment thereof.

Nucleic acids that are complementary to or hybridize to all or a unique fragment of the novel MRP-β gene can be used as antisense or primer oligonucleotides. Antisense oligonucleotides disrupt gene expression and/or protein production and thereby attenuate an aberrant phenotype attributable to inappropriate expression or activation of the target gene. Lautier et al. (1996), 52 Biochem. Pharmacol. 967–977. As a result, the phenotype is abrogated or its penetrance is diminished (attenuated). Therapeutic intervention to attenuate a multidrug-resistance phenotype, for example, restores cellular vulnerability to cytotoxic drugs. Smyth et al. (1996), PCT Publ. WO 96/02556, teaches that antisense oligonucleotides disrupt expression of the target gene by interfering with gene transcription, transcript splicing, or translation; by triggering enzymatic destruction by RNAse H; or by destroying the target through one or more reactive moieties incorporated into the antisense compound. Preferred oligonucleotides herein have sequences sufficiently complementary to all or a unique fragment of the MRP-β gene to hybridize, under intracellular conditions, to the gene's coding or noncoding strand, or to an RNA transcript of the gene. Optionally, the oligonucleotide can be designed to hybridize to a polypeptide coding region, or to a 5' or 3' untranslated region of the gene or gene transcript, or to a gene intron or an intron/exon boundary. Typically, the present oligonucleotides are at least 9 nucleotides in length, and range from about 12 to about 40 bases in length, and are generally about 16 to 30 bases in length, with about 20 bases being considered optimal. Exemplary oligonucleotides are at least 15, 21, or 24 nucleotides in length. Specific examples of the present oligonucleotides are set forth in SEQ ID Nos: 4, 5, 6, 7 and 8. These and other exemplary oligonucleotides can be synthesized readily by conventional techniques.

While either DNA or RNA is suitable for use in primer, probe or antisense oligonucleotides, it is often desirable to include one or more modified bases, backbone sugar moieties, or backbone linking groups. Thus, Smyth et al. (1996) teaches that alkylphosphonates, phosphorothioates, phosphorodithioates, phosphate esters, alkylphosphonothioates, phosphoramidates, carbamates, carbonates, phosphate triesters, acetamidate, 2-O-methyls, and carboxymethyl esters all are suitable for use in the context of antisense oligonucleotides. Preferred modified olignoculeotides herein comprise a modified backbone structure. Peptide nucleic acid (PNA) oligonucleotides prepared according to the teachings of Perry-O'Keefe et al. (I 996), 93 Proc. Nat'l. Acad. Sci. USA 14670–14675, and Egholm et al. (1993), 365 Nature 566–568, are particularly preferred herein.

In addition, the invention encompasses all MRP-β nucleic acids having sequences at least 50% identical to SEQ ID No: 1 or to the complement thereof. The determination of whether a particular sequence meets this criterion is made using the TBLAST N algorithm according to the teachings of Altschul et al. (1990), 215 J. Mol. 403–410, the teachings of which are incorporated herein by reference. Such nucleic acids encode variants, which may be nat lly-occurring or biosynthetic, of the MRP-βpolypeptide disclosed herein.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). The determination of percent homology between two sequences can be accomplished using a mathematical algorithim. A preferred, non-limiting example of a mathematical algorithim utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs of Altschul, et al. (1990) J. Mol. Biol. 215:403–10. BLAST nucleotide searches can be performed with the NBLAST program, score=100, wordlength=12 to obtain nucleotide sequences homologous to D6 nucleic acid molecules of the invention. BLAST protein searches can be performed with the XBLAST program, score=50, wordlength=3 to obtain amino acid sequences homologous to D6 protein molecules of the invention. To obtain gapped alignments for comparison purposes, Gapped BLAST can be utilized as described in Altschul et al., (1997) Nucleic Acids Research 25(17) :3389–3402. When utilizing BLAST and Gapped BLAST programs, the default parameters of the respective programs (e.g., XBLAST and NBLAST) can be used. See, for example, the National Centers for Biotechnology Information website which is linked to the National Library of Medicine website (www.ncbi.nlm.rih.gov). Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

Similarly, the invention encompasses all nucleic acids which, by virtue of the well-known degeneracy of the genetic code, also encode the SEQ ID No: 2 polypeptide. Such degenerate variants may be naturally-occurring or may be produced through routine application of molecular engineering techniques. Current Protocols in Molecular Cloning, Ausubel et al., eds. (1989), Greene Publishing and Wiley Interscience, New York, N.Y. and in Sambrook et al. (1989), Molecular Cloning A Laboratory Manual, 2nd ed., Cold Spring Harbor Laboratory Press, Cold Spring Harbor, N.Y. Furthermore, the invention encompasses all nucleic acids encoding polypeptides having sequences that share at least 75% sequence similarity with the disclosed MRP-β polypeptide. Similarity is calculated generally according to the method of Altschul et al. (1990), 215 J. Mol, Biol, 403–410, using the TBLAST P algorithm. Moderate gaps or insertions of amino acid residues are ignored for similarity calculation purposes. Preferably, the MRP-β variants encoded by these nucleic acids function similarly to MRP-β when expressed by a host cell produced as described herein. That is, preferred MRP-β variant polypeptides are displayed on the surface of a host cell and contribute to the cell's acquisition of a multidrug-resistance phenotype. MRP-β variants thus may differ from that comprising SEQ ID No: 2 by the presence of one or more amino acid insertions, deletions, or point substitutions. Deletion variants are expected to facilitate investigation into the minimum MRP-β polypeptide structure required to support drug transport and thus multidrug-resistance phenotype. Substitution variants are expected to facilitate investigation into the mechanism and specificity of MRP-β function. Exemplary substitution variants include chimeric polypeptides in which one or more MRP-β amino acid residues are replaced by the corresponding residue in either the MRP or P-glycoprotein sequence. All nucleic acids encoding such variants are within the scope of the present invention. All oligonucleotides complementary to, or which hybridize to, the present nucleic acids are within the scope of this invention.

All of the foregoing nucleic acids of the present invention can be produced, expressed, and/or manipulated by conventional molecular engineering techniques such as the techniques set forth in *Current Protocols in Molecular Cloning*, Ausubel et al., eds. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y., and the teachings described and referenced in Watson et al. (1992), *Recombinant DNA*, 2nd ed., Scientific American Books and W. H. Freeman & Co., New York, N.Y.

Any of the foregoing nucleic acids can be inserted into an expression vector by routine molecular engineering techniques. *Current Protocols in Molecular Cloning*, Ausubel et al., eds. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y., and publications referenced in Watson et al. (1992), *Recombinant DNA*, 2nd ed., Scientific American Books and W. H. Freeman & Co., New York, N.Y. Preferred expression vectors thus encode full-length or unique fragment MRP-β polypeptides. Particularly preferred are expression vectors that, when expressed in a suitable host cell, contribute to the emergence of a multidrug-resistance phenotype therein. In other embodiments, the vector comprises DNA or RNA complementary to an antisense oligonucleotide. The present expression vectors further comprise one or more conventional expression control elements, such as an enhancer, promoter, initiation site, or termination site operatively associated with the inserted MRP-β nucleic acid. Non-limiting examples of suitable expression control elements include the cytomegalovirus immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoter of acid phosphatase, the promoters of yeast α-mating factors, and immunoglobulin enhancers and/or promoters. Optionally, the expression vector may comprise a selection marker, such as an antibiotic resistance gene. Single or multiple copies of the inserted MRP-β nucleic acid can be encoded by the vector. Preferably, for production of eukaryotic (preferably mammalian) host cells, or for therapeutic purposes, the vector is retroviral in origin or comprises one or more retroviral elements. The vector can be taken up (internalized) by cells via transfection, infection, microinjection, pinocytosis or in the course of cell division, or can be packaged, e.g., in a liposome or retroviral envelope. In this manner, the vector can be designed for selective internalization in dividing cells, transformed cells, or in cells of a tissue type susceptible to retroviral infection. Deeley et al. (1996), U.S. Pat. No. 5,489,519, the teachings of which are incorporated herein by reference, summarizes conventional techniques for the preparation of expression vectors.

The present MRP-β expression vectors are suitable for use in any conventional host cell transfection technique, e.g., as described in *Current Protocols in Molecular Cloning*, Ausubel et al., eds. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y., and in publications referenced in Watson et al. (1992), *Recombinant DNA*, 2nd ed., Scientific American Books and W. H. Freeman & Co., New York, N.Y. Thus, the present invention further provides a host cell that produces an MRP-β polypeptide or an MRP-βantisense oligonucleotide. Preferred host cells display an MRP-β polypeptide on the cell surface and/or display a multidrug-resistance phenotype. Such host cells are expected to facilitate elucidation of the types or structural classes of chemotherapeutic drugs or other substances ejected or sequestered from the intracellular milieu by MRP-β. Thus, MRP-β host cells allow rapid, in vitro evaluation of the specific characteristics of the multidrug-resistance phenotype associated with MRP-β expression or overexpression. Such cells further allow production of MRP-β polypeptides and antibodies as described below.

Cells (source cells) suitable for the production of the foregoing host cells include, but are not limited to, primary or immortalized epithelial cells such as carcinoma cells or cell lines. Additional source cells include primary or immortalized mesenchymal cells, such as sarcoma cells. Still further suitable cells include hematopoietic system cells, such as leukemia, lymphoma or lymphosarcoma cells. Mammalian or non-mammalian cells can be used, but in general, mammalian (e.g., murine, ovine, porcine, bovine or, preferably, human) cells are preferred. For certain purposes, such as the rapid phenotypic characterization of deleterious phenotypes (e.g., multidrug resistance phenotypes) conferred by MRP-β alteration, expression or overexpression, or such as the rapid screening of candidate modulators of MRP-β, non-mammalian cells such as insect cells or yeast cells, also may be used. In all circumstances, the identification of transfectants (newly produced host cells) is dependent on the use of source cells that are vulnerable to the cytotoxic effects of drugs transported by MRP-A or metabolized by the product of a selection marker gene optionally included in the vector.

Deeley et al. (1996), 5,489,519, Cole et al. (1994), 54 *Cancer Res.* 5902–5910, and Stride et al. (1995), 49 *Mol. Pharmacol.* 962–971, each describe the transfection of human HeLa cells with MRP to produce an MRP expressing host cell. Engel et al. (1996), U.S. Pat. No. 5,556,856, and Zelle et al. (1996), U.S. Pat. No. 5,543,423, describe the transfection of murine leukemia cells with MDR-1 to produce P-glycoprotein expressing host cells. Sarkadi et al. (1995), PCT Publ. WO9531474 describes the transfection of murine NIH 3T3 fibroblasts and of *Spodoptera frugiperda* (insect) cells with MDR-1 to produce P-glycoprotein expressing host murine and insect cells, respectively. Ruetz et al. (1996), 271 *J. Biol, Chem,* 4154–4160, describes the transfection of *Saccharomyces cerevisiae* (yeast) with MRP and MDR-1 to produce yeast host cells. Any of the above-mentioned, available source cells can be transfected according to standard techniques with an MRP-β expression vector to produce MRP-βexpressing host cells. Relevant techniques are disclosed in the above-cited references and in *Current Protocols in Molecular Cloning*, Ausubel et al., eds. (1989), Greene Publishing and Wiley Interscience, New York, N.Y. Currently, the immortalized MCF-7 human breast adenocarcinoma cell line, available from the American Type Culture Collection as ATCC No. HTB22, is a preferred source cell. An exemplary standard transfection technique suitable for use with MCF-7 is the lipofectin technique summarized in Cole et al. (1994), however, many conventional alternatives (e.g., calcium phosphate; lithium acetate; baculoviral or retroviral infection) are available and can be used with the MCF-7 or other exemplary source cell lines. After transfection, transfectants can be identified by culturing the cells in the presence of hygromycin B (as in Cole et al. (1994)) or another selection toxin, such as bisantrene or adriamycin (doxorubicin). Expression of a biologically-functional MRP-β polypeptide can be confirmed by analyzing cellular RNA for the presence of vector-derived MRP-β transcripts; by analyzing cellular protein for the presence of an epitope unique to, MRP-β; by analyzing the cell surface for display of an epitope unique to MRP-β; or, by analyzing whether the cell has acquired an MRP-β associated phenotype, such as a multidrug-resistance phenotype.

The present host cells initially are expected to facilitate production of MRP-β polypeptides and structural and functional analysis thereof. The MRP-β polypeptide comprising SEQ ID No: 2 is expected to bind ATP, and to be an integral, multispanning transmembrane protein generally as described in Almquist et al. (1995), 55 *Cancer Res.* 102–110. A significant portion of the total MRP-β produced in host cells is expected to span the cells' plasma membrane, with an additional portion being present intracellularly, e.g., in the endoplasmic reticulum and/or the Golgi apparatus. Thus, MRP-β host cells are expected to display extracellular portions of the multispanning MRP-β polypeptide on the cell surface, appropriately configured to mediate the ATP-dependent sequestration or export (efflux) of a plurality of cytotoxic drugs, including drugs conventionally used as chemotherapeutic agents. These general properties are deduced from an assessment of the primary structure (sequence) of the MRP-β polypeptide. MRP-β is considered to be a novel member of the ABC Transporter Protein superfamily and is deemed likely to contribute to multidrug-resistance phenotypes by mediating drug transport across cellular phospholipid membranes. FIG. 2A-F sets forth an exemplary sequence alignment of the disclosed novel MRP-β polypeptide (SEQ ID No: 2), with relevant sequence of the MRP polypeptide of Deeley et al. (1996), U.S. Pat. No. 5,489,519 (SwissProt P33527, 1531 aa). The alignment was generated using the ALIGN algorithm (which calculates a global alignment of two sequences), version 2.0 (Myers and Miller (1989) CABIOS), scoring matrix: PAM120, gap penalties: −12/−4, 30.9% identity, global alignment score: 1214.

The present host cells provide an appropriate purification source for obtaining useful quantities of MRP-β polypeptide. The polypeptide can be isolated in substantially pure form (i.e., essentially free of detectable levels of non-MR-β polypeptides or other cell components) by an appropriate combination of one or more protein extraction or purification techniques such as those described in Sambrook et al. (1989), *Molecular Cloning A Laboratory Manual,* 2nd ed., Cold Spring Harbor Laboratory Press, Cold Spring Harbor, N.Y. Alternatively, an MRP-β enriched subcellular membrane preparation can be obtained by suitable cell disruption and fractionation techniques, all of which are well-known in the art. An exemplary, adaptable protocol for obtaining an MRP enriched subcellular membrane preparation is set forth in Zaman et al. (1994), 91 *Proc. Natl. Acad. Sci. USA* 8822–8826. Intact host cells, MRP-β enriched membrane preparations thereof, and/or isolated MRP-β protein can be used for a number of purposes, such as the production of monoclonal or polyclonal antibodies, characterization of substrates affected by MRP-β biological function, and identification of novel modulators (e.g., inhibitors) affecting MRP-β biological function.

Antibody production involves administration of one or more immunogenic doses of an MRP-β polypeptide preparation (whether isolated or incorporated in a cell membrane) to an appropriate non-human animal, such as a mouse, rat, rabbit, guinea pig, turkey, goat, sheep, pig, or horse. To enhance immunogenicity, the preparation can be emulsified with a conventional adjuvant, such as Freund's complete or incomplete adjuvant. Routine monitoring of serum immunoglobulins, using peripheral blood samples withdrawn at appropriate intervals (e.g., seven to ten days) after an initial or subsequent immunization, can be used to detect the onset and/or maturation of a humoral immune response. Detection and, optionally, quantitation, of immunoglobulins selectively reactive with an MRP-β epitope can be achieved through any conventional technique, such as ELISA, radioimmunoassay, Western blotting, or the like. Appropriate means of eliciting and monitoring production of antibodies with selective reactivity (binding) for other multidrug-resistance associated proteins are disclosed in Arceci et al. (1994), U.S. Pat. No. 5,369,009, which is incorporated herein by reference. An immunoglobulin "selectively reactive with an MRP-β epitope" has, binding specificity for the recognized epitope such that an antibody/epitope complex forms under conditions generally permissive of the formation of such complexes (e.g., under conditions of time, temperature, ionic strength, pH, ionic or nonionic detergent, carrier protein, etc.). Serial dilution (titration) analysis by standard techniques is useful to estimate the avidity of antibodies in the immune serum sample for one or more epitopes unique to MRP-β. As defined herein, an "epitope unique to MRP-β" is a unique, immunogenic fragment of the full-length MRP-β polypeptide. A unique linear epitope typically ranges in size from about ten to about twenty-five amino acid residues, and frequently is about twelve to eighteen residues in length. Unique conformational epitopes also are provided herein, and comprise two or more unique fragments of the MRP-β polypeptide that, due to their juxtaposition in the folded polypeptide, form a single immunogenic epitope.

Immune serum having a high titer generally is preferred herein. Serum having a half-maximal avidity for a unique MRP-β epitope of at least about 1:1000, preferably at least about 1:110,000, can be harvested in bulk for use as a source of polyclonal antibody useful in the detection and/or quantitation of MRP-β. Polyclonal immunoglobulins can, if desired, be enriched by conventional fractionation of such serum, or can be isolated by conventional immunoadsorbent techniques, e.g., using a Protein A or Protein G chromatography resin. Immune, high titer murine or guinea pig serum alternatively is preferred herein for the production and screening of hybridomas secreting monoclonal antibodies selectively reactive with MRP-β. The present hybridomas can be produced according to well-known, standard techniques. The present monoclonal antibodies can be obtained from hybridoma culture supernatant, or from conventionally produced ascites fluid, and optionally isolated via immunoadsorbent chromatography or another suitable separation technique prior to use as agents to detect and/or quantitate MRP-β.

A preferred antibody, whether polyclonal or monoclonal, is selectively reactive with a unique MRP-β epitope that is displayed on the surface of MRP-β expressing cells, such as a host cell as provided herein. The preferred antibody accordingly can be used to detect and, if desired, quantitate MRP-β expressing cells, e.g., normal or transformed cells in a mammalian body tissue or biopsy sample thereof. Exemplary analogous methods for the use of antibodies reactive with epitopes unique to P-glycoprotein are disclosed in Arceci et al. (1994), U.S. Pat. No. 5,369,009; exemplary analogous methods for the use of antibodies reactive with epitopes unique to MRP are disclosed in Deeley et al. (1996), U.S. Pat. No. 5,489,519. Both disclosures are incorporated herein by reference. Specifically, the preferred antibody can be used to detect MRP-β expressing cells whether such cells are host cells or mammalian body tissue cells that aberrantly express MRP-β as a result of exposure to a selection toxin such as a chemotherapeutic drug. Advantageously, intact, e.g., living, cells that display a unique MRP-β epitope can be detected by standard immunohistochemical, radiometric imaging or flow cytometry techniques. The present antibody can be used to detect and/or monitor MRP-β polypeptide production in lieu of or in addition to detecting MRP-β gene expression using the novel MRP-β nucleic acids provided herein. Thus, the antibody can be used to assess whether an aberrant phenotype, such as a multidrug-resistance phenotype, in a given cell population is associated with cell surface display of MRP-β. Further, the antibody can be used to assess the natural tissue-specific production of MRP-β, and thus to assess tissues likely to give rise to multidrug-resistant carcinomas or sarcomas. In addition, the present antibody can be used to monitor tumor biopsy samples to provide information relevant to selecting or revising a course of disease management, or to diagnosis, prognostication and/or staging of any disease associated with an abnormality affecting MRP-β. An exemplary disease is proliferative neoplastic disease. Furthermore, the present antibody can be used in a cell-sorting procedure or other cell isolation procedure to generate a substantially pure preparation of MRP-β expressing cells, or a cell population substantially depleted of MRP-β expressing cells. Each of the foregoing can be achieved through routine practice or modification of well-known techniques, including but not limited to the conjugation of a detectable moiety (e.g., a radionuclide, fluorophore, chromophore, binding pair member, or enzyme) to the MRP-β reactive antibody.

A hybridoma secreting an MRP-β reactive monoclonal antibody of the present invention additionally provides a suitable source of nucleic acid for the routine construction of a fusion polypeptide comprising an antigen-binding fragment derived from the MRP-β reactive antibody. The present fusion polypeptide can be prepared by routine adaptation of conventional techniques therefor in Deeley et al. (1996), U.S. Pat. No. 5,489,519 (incorporated herein by reference). The fusion polypeptide can be a truncated immunoglobulin, an immunoglobulin having a desired constant region (e.g., IgG in lieu of IgM), or a "humanized" immunoglobulin having an MRP-β reactive Fv region fused to a framework region of human origin. Additional fusion polypeptides can comprise, in addition to an MRP-β reactive antigen-binding fragment, a non-immunoglobulin polypeptide such as a cytotoxic polypeptide (e.g., diphtheria toxin, ricin) or a chemoattractant polypeptide that stimulates immune effector cells (cytotoxic T cells, natural killer cells, macrophages) to kill cells that display MRP-β. Standard techniques well-known in the art can be used to produce appropriate immunoglobulin fusion polypeptides of the present invention.

The foregoing compositions can be used for a number of purposes, including the assessment (e.g., for diagnostic purposes) of abnormalities in the structure and/or expression of a cellular MRP-β gene. Thus, for example, the invention provides a method for detecting an abnormality in a cellular MRP-β gene, such as a mutation arising in germline or somatic cellular genomic DNA. Similarly, the present method provides a means for detecting chromosomal rearrangement, restriction fragment polymorphism, allelic loss or disruption of a native methylation pattern in the MRP-β gene. This method exploits the hybridization properties of an oligonucleotide probe or primer described herein. A preferred oligonucleotide is modified by the presence of a detectable label and/or a peptide nucleic acid backbone. Such oligonucleotides, which hybridize to one or more unique fragments of a cellular MRP-β gene suspected of harboring a structural (e.g., sequence) abnormality, can be used in a diagnostic protocol as disclosed in Perry-O'Keefe et al. (1996); 93 Proc. Nat'l. Acad. Sci. USA 14670–14675, or as disclosed in Ravnik-Glavac et al. (1994), 3 Hum. Mol. Biol. 801——. Other nucleic acid-based diagnostic methods that can be exploited for purposes of assessing MRP-β gene abnormalities are as set forth in Myers et al. (1985), 230 Science 1242; Cotton et al. (1988), 85 Proc, Nat'l. Acad. Sci. USA 4397; Suleeba et al. (1992), 217 Meth. Enzymol 286–295; Orita et al. (1989), 86 Proc, Nat'l. Acad. Sci. USA 2766; Cotton et al. (1993), 285 Mutat. Res. 125–144; Hayashi (1992), 9 Genet. Anal. Tech. Appl. 73–79; and, Myers et al. (1985), 313 Nature 495. Additional methods are based on selective amplification and/or extension of MRP-β PCR primers, e.g., as described in Landegran et al. (1988), 241 Scienc 1077–1080; Nakazawa et al. (1994), 91 Proc. Nat'l. Acad. Sci. USA 360–364; and Abravaya et al. 91995), 23 Nucl. Acids Res. 675–682, and in publications referenced in Watson et al. (1992), Recombinant DNA 2nd ed., Scientific American Books and W.H. Freeman & Co., New York, N.Y.

Additional diagnostic and/or characterization methods using nucleic acid compositions provided herein include Northern blot, slot blot or similar methods for visualizing fluctuations, especially abnormal overproduction, in the level of cellular transcripts comprising MRP-β sequences. These methods rely on the use of MRP-β oligonucleotide probes and hybridization conditions appropriate for the formation of probe/RNA hybrids. Exemplary conditions for use with nucleic acid or modified nucleic acid probes are as set forth in Perry-O'Keefe et al. (1996), 93 Proc. Nat'l. Acad. Sci. USA 14670–14675; Current Protocols in Molecular Cloning, Ausubel et al., eds. (1989), Greene Publishing and Wiley Interscience, New York, N.Y. and Sambrook et al. (1989), Molecular Cloning: A Laboratory Manual, 2nd ed., Cold Spring Harbor Laboratory Press, Cold Spring Harbor, N.Y. An exemplary transcript hybridization protocol is set forth in EXAMPLE 2 herein. This example confirms the association of MRP-0 expression with the occurrence of a multidrug-resistance phenotype transformed cell populations. Similar confirmation can be obtained by comparing a normal cell population with a tissue-matched transformed multidrug resistant population. Preferably, the cell populations each are derived from an exemplary mammalian body tissue, such as an epithelial tissue (e.g., mammary, respiratory tract, gastrointestinal tract, urogenital tract, paracrine, endocrine or neuroendocrine tissue). EXAMPLE 2 demonstrates that MRP-β expression is significantly elevated in multidrug-resistant derivatives of well-known cell fines, including the MCF-7 breast adenocarcinoma cell line, the HL60 promyelocytic leukemia cell line, the A2780 ovarian carcinoma cell line, and the U937 myeloid leukemia cell line. Thus, MRP-β expression level correlates with the occurrence of multidrug-resistance rather than with derivation from a particular body tissue type.

Cellular MRP-β gene expression level similarly is expected to correlate with the maintenance or reappearance of multidrug resistance in transformed cells in situ following exposure to one or more chemotherapeutic drugs, or to a conventional chemosensitizer or "MDR reversal" agent. In other words, MRF-β gene expression activation or transcript stabilization is deemed likely to provide transformed cells with a selective advantage that is distinct from the advantage (s) derivable from P-glycoprotein or MRP expression. As a result, the monitoring of MRP-β transcript or polypeptide production, or gene expression level, or fluctuations therein, in one or more tumor biopsy samples is expected to provide information relevant to diagnosis, prognostication and/or staging of neoplastic disease in a cancer sufferer. Any suitable means for detecting MRP-β transcript or polypeptide production or stabilization, or gene expression level, can be applied for the present diagnostic purposes. Thus, gene expression can be monitored using any appropriate nucleic acid based method described above. MRP-β polypeptide production or accumulation can be monitored using an MRP-β antibody described herein. Any appropriate conventional method for visualizing selective binding of an antibody to its cognate epitope may be used. Appropriate methods are described in Sambrook et al. (1989), *Molecular Cloning: A Laboratory Manual,* 2nd ed., Cold Spring Harbor Laboratory Press, Cold Spring Harbor, N.Y.

In some embodiments, diagnosis is achieved by hybridization techniques involving the use of a modified MRP-β probe as described herein. A preferred technique involved the use of a peptide-nucleic acid probe as described in Egholm et al. (1993), 365 *Nature* 566–568, and Perry-O'Keefe et al. (1996), 93 *Proc. Natl. Acad. Sci. USA* 14670–14675. Thus, for example, the protocol of EXAMPLE 2 can be routinely adapted to allow assessment of multidrug-resistant transformed cells that have survived exposure in situ to a chemosensitizer or to an agent that interferes with P-glycoprotein or MRP expression. Further exemplary demonstrations can be produced by routinely adapting the EXAMPLE 2 protocol to the assessment of two or more biopsy samples obtained from an individual (e.g., a cancer sufferer) at different times. Preferably, a first biopsy sample corresponds to a time of diagnosis or to a time prior to or concomitant with the onset of chemotherapy. A second biopsy sample corresponds to a timepoint at which beneficial results of chemotherapy are expected to be detectable (e.g., a time sufficiently following the onset of chemotherapy for cytotoxic effects to be observed). One or more subsequent biopsy samples may correspond to further timepoints optionally correlated with fluctuations in clinical parameters (e.g., relapse, remission, a change in disease staging, or the like). Changes (fluctuations) in MRP-β gene expression, transcript stabilization, polypeptide production, and/or polypeptide stabilization are expected to correlate with, or to predict, the emergence or attenuation of a deleterious phenotype associated with MRP-β, such as a multidrug-resistance phenotype.

It will be appreciated that the causes of multidrug-resistance phenotypes vary with each individual cell type and are not wholly accounted for by expression or overexpression of P-glycoprotein, MRP or the novel MRP-β disclosed herein. Rather, additional members of the ABC Transporter Protein family may be involved, as may be one or more members of known or novel signal tranduction pathways or intracellular metabolic or growth-regulatory pathways. The present discovery of MRP-β facilitates investigation into the role(s) of such additional gene expression products in the acquisition and/or maintenance of a multidrug-resistance phenotype. Specifically, the discovery of MRP-β provides an improved method of identifying a gene, especially a hitherto unknown gene, expression of which contributes to emergence or maintenance of drug-resistant phenotype in transformed mammalian cells.

The identification method is an adaptation of the differential display technique disclosed in Liang et al. (1997), U.S. Pat. No. 5,599,672 and Pardee et al. (1993), U.S. Pat. No. 5,262,311. The method involves the steps of providing a transformed or normal cell population (the first population) derived from an exemplary mammalian tissue, such as a secretory epithelium (a nonlimiting example of which would be mammary epithelium), and culturing the cell population in the presence of a selection toxin, such that a drug-resistant derivative population (the second population) is produced. Mirsky et al. (1987), 47 *Cancer Res.* 2594–2598, provides an exemplary protocol for selecting a drug-resistant derivative of an immortalized human small cell lung carcinoma cell line, H69. This exemplary protocol can be adapted to use with additional cell lines, or with primary cells in culture. Thus, Hait et al. (1992), U.S. Pat. No. 5,104,858, teaches the stepwise selection of a doxorubicin-resistant derivative of the well-known MCF-7 breast adenocarcinoma cell line. Further adaptations include, e.g., the use of a selection toxin other than adriamycin. Powell et al. (1995 and 1996), U.S. Pat. Nos. 5,387,685, 5,550,149 and 5,561, 141, teaches the use of bisantrene to select for a multidrug-resistant derivative of the known human ovarian carcinoma cell line, OVCAR-3 (HTB-161). If desired, the first and second populations can be selected from well-known cell lines and/or available multidrug-resistant derivatives thereof. Sunkara (1996), U.S. Pat. No. 5,523,304, teaches the use of a multidrug-resistant human epidermoid carcinoma cell line, KBV1. Ramu et al. (1993), U.S. Pat. No. 5,190,946, teaches the use of a murine leukemia cell line (P388) and an available multidrug-resistant derivative thereof (P388/ADR). Alternatively, the populations can be selected from biopsy samples withdrawn from an individual (e.g., a cancer sufferer) before and after a clinical observation of multidrug resistance. Currently, the MCF-7 cell line and multidrug-resistant derivatives thereof are considered exemplary and are preferred for analysis of multidrug-resistance phenotypes.

Expressed nucleic acids (transcription products; RNA) are isolated separately from the first and second populations, and fractionated by electrophoretic resolution or another conventional technique as described in Liang et al. (1997), U.S. Pat. No. 5,599,672. Alternatively, the expression products of the first population are used as an adsorbent to deplete the expression products of the second population of individual transcripts that are common to both populations. Thereafter, the resolved expression products are analyzed to identify one or more gene transcripts that are preferentially expressed, underexpressed or overexpressed in the second population. Such gene transcripts accordingly are associated with the multidrug-resistance phenotype. One or more probes complementary to the novel MRP-β nucleic acids disclosed herein thus can be used as an internal control to monitor successful identification of multidrug-resistance associated gene transcripts. Of course, probes complementary to nucleic acids encoding P-glycoprotein and/or MRP can be used similarly. Multidrug-resistance associated gene transcripts that are identified in this adaptation of the Liang et al. (1996) method are subjected to routine sequencing and, if previously unknown (or unknown to be correlated with multidrug-resistance) may be cloned according to conventional molecular engineering techniques as described in

*Current Protocols in Molecular Cloning*, Ausubel et al., eds. (1989), Greene Publishing and Wiley Interscience, New York, N.Y. In this manner, the MRP-β probes and/or primers described herein can be used as research tools to identify and/or produce clones of hitherto unknown genes that contribute to multidrug-resistance phenotypes, such as genes that regulate cellular expression of P-glycoprotein, MRP and/or MRP-β.

The compositions provided as a result of this invention furthermore are useful tools for the characterization of MRP-β polypeptide structure, biological function and regulation in normal mammalian cells and body tissues. The availability of information concerning the biological role of MRP-β is expected to facilitate the design, production and use of therapeutic agents to treat abnormal phenotypes, particularly disease-related phenotypes, contributed to by aberrancies in MRP-β. As part of this characterization effort, the natural expression pattern of MRP-β was surveyed in diverse mammalian body tissues. Expression products (total or poly-A(+) RNA) derived from a plurality of human body tissues were screened for hybridization with a unique MRP-β probe fragment as described in EXAMPLE 3. Transport or secretion function attributable to MRP-β was expected to affect gene expression in cells and/or tissues responsible for the secretion or excretion of cellular products or metabolites. MRP-β was observed to be expressed, at least at low (detectable baseline) levels, in substantially all body tissues. MRP-β expression similarly can be surveyed in cell types characteristic of a particular body tissue. For this more refined survey, cell types can be enriched and/or isolated from intact body tissues by convention mincing, homogenization, collagenase or trypsin digestion procedures, followed by filtration, sedimentation, adherence or panning procedures well known in the art. Alternatively, cell cultures or cell lines derived from specific body cell types may be used.

Inappropriate alteration of a cellular MRP-β gene, aberrant gene expression, transcript stabilization, or inappropriate biological function or stabilization of an MRP-β polypeptide is expected to correlate generally with tissue or cell types with a known propensity for generating transformed cells with inherent or readily acquired multidrug-resistance, especially multidrug-resistance that is refractory to treatment with known chemosensitizing agents or MDR reversal agents. MRP-β production or activity accordingly is likely to fluctuate in secretory epithelial tissues, e.g., respiratory tract, gastrointestinal tract, mammary, urogenital tract, paracrine, endocrine, and neuroendocrine tissues. Sarcomas, carcinomas, especially adenocarcinomas, originating from such tissue, particularly those originating from lung, colon, kidney, bladder, breast, ovarian, uterine, cervical, testicular, prostate or pancreatic tissue, similarly are expected to inappropriately produce MRP-β and to display or acquire multidrug-resistance phenotypes. Indeed, confirmation of such fluctuations already has been obtained, in EXAMPLE 2.

Abnormal or aberrant phenotypes, especially multidrug-resistance associated phenotypes, that are contributed to by abnormalities affecting MRP-β, can be treated using pharmaceutical or therapeutic compositions provided herein. More specifically, the invention provides therapeutic compositions, including prophylactic, palliative and remedial compositions, useful for treatment of any disease state or deleterious condition contributed to by an abnormality affecting MRP-β. A first category of such therapeutic compositions comprise an antisense oligonucleotide, or a vector encoding an antisense oligonucleotide, that hybridizes to nucleic acid corresponding to or transcribed from a cellular MRP-β gene. Stewart et al. (1996), 51 *Biochem, Pharmacol* 461–469, and Baracchini et al. (1996), U.S. Pat. No. 5,510,239, report successful, antisense-mediated attenuation of an UP multidrug-resistance phenotype in cultured H69AR cells: exposure to antisense oligonucleotides significantly reduced intracellular MRP transcript and polypeptide levels. The techniques and administration methods disclosed therein can be adapted to provide antisense-mediated attenuation of an MRP-β phenotype as disclosed herein. Stewart et al. (1996) report, however, that attenuation was achieved only transiently, due to the rate of cellular production of new MRP gene transcripts and/or degradation of the antisense oligonucleotide. Stewart et al. (1996) notes that, in the adriamycin selected multidrug-resistant H69AR cells, the phenotype cannot be attributed entirely to MRP expression, and for this reason counsels that antisense oligonucleotides should be used that are complementary to gene regions known to be conserved among members of the ABC Transporter Protein family. Similarly, Smyth et al. (1996), PCT Publ. WO 96/02556, reports successful, antisense oligonucleotide mediated, attenuation of a P-glycoprotein based multidrug resistance phenotype in cultured cells wherein the phenotype arises solely from P-glycoprotein production. By their nature, antisense oligonucleotides are limited to disruption of their specific target genes. Thus, the desired result of phenotypic attenuation will not be achieved where the multidrug resistance phenotype arises from (or is preserved by) expression of one or more previously unknown genes, to which the antisense oligonucleotide is unable to hybridize effectively under intracellular conditions.

This limitation is emphasized by the disclosure herein of the present novel MRP-β. However, the present disclosure provides basis for the design and construction of the present novel antisense oligonucleotides (and oligonucleotide analogs comprising one or more of the modifications mentioned in Smyth et al. (1996)) competent to hybridize, under intracellular conditions, to all or a unique portion of the MRP-β gene or a transcript thereof. The present antisense oligonucleotides can be used alone or formulated as a cocktail together with one or more of the above-mentioned antisense oligonucleotides specific to MRP or the MDR-1 gene. Antisense oligonucleotides specific for MRP-β can be produced by conventional synthetic or biosynthetic techniques, and formulated together with pharmaceutically acceptable carriers and/or excipients into antisense pharmaceutical compositions suitable for local or systemic administration to an individual, e.g., a cancer sufferer. Suitable pharmaceutical carriers and routes of administration are described in Baracchini et al. (1996), U.S. Pat. No. 5,510,239, and Deeley et al. (1996), U.S. Pat. No. 5,489,519, the teachings of each of which are incorporated herein by reference.

The present MRP-β antisense oligonucleotides accordingly can be used to attenuate any undesirable phenotype associated with MRP-β, such as but not limited to a multidrug-resistance phenotype attributable in whole or in part to MRP-β expression or overexpression, e.g., in transformed cells in situ in mammalian body tissue. The present antisense oligonucleotides thus make possible a novel method of potentiating chemotherapy to eradicate multidrug-resistant transformed cells from the body of a mammal. The effectiveness of chemotherapy is "potentiated" (enhanced) by restoring or improving vulnerability of the transformed cells to the cytotoxic effects of a chemotherapeutic drug that otherwise would be ejected from the cell. The method involves administering the desired chemotherapeutic drug to an individual afflicted with a multidrug-resistant transformed cell population (a tumor, e.g., a carcinoma, sarcoma, leukemia, lymphoma or lymphosarcoma), and coadministering an above-described antisense pharmaceutical composition. The administration and coadministration steps can be carried out concurrently or in any order, and can be separated by a time interval sufficient to allow uptake of either compound by the transformed cells to be eradicated. For example, the present antisense pharmaceutical composition (or a cocktail composition comprising an MRP-β antisense oligonucleotide in combination with one or more other antisense oligonucleotides) can be administered to the individual sufficiently in advance of administration of the chemotherapeutic drug to allow the antisense composition to permeate the individual's tissues, especially tissue comprising the transformed cells to be eradicated; to be internalized by transformed cells; and to disrupt MRP-β gene expression and/or protein production. The time interval required can be determined by routine pharmacokinetic means, and should be expected to vary with age, weight, sex, lean tissue content, and health status of the individual, as well as with size and body compartment location of the population of multidrug-resistant transformed cells to be eradicated.

Similar parameters should be considered in selecting a route of administration of the antisense pharmaceutical composition. Thus, the composition may be administered locally or systemically, preferably by a parenteral route. The composition can be administered intravenously, intraperitoneally, retroperitoneally, intracisternally, intramuscularly, subcutaneously, topically, intraorbitally, intanasally or by inhalation, optionally in a dispersable or controlled release excipient. One or several doses of the present composition may be administered as appropriate to achieve uptake of a sufficient amount of the present antisense oligonucleotide to produce an attenuation of multidrug-resistance phenotype in the transformed cells to be eradicated by chemotherapy.

The foregoing method alternatively can be accomplished by administration of a suitable expression vector encoding the present MRP-β antisense oligonucleotide. Use of the present vector to internally produce or overproduce the present antisense oligonucleotide is expected to overcome the limitation noted in Stewart et al. (1996), namely, to ensure a continuous or renewable level of oligonucleotide mediated disruption of MRP-β expression or production. In this manner, the multidrug-resistance phenotype can be attenuated, if necessary, for a sufficient period of time for the coadministered chemotherapeutic agent to cause the death of transformed cells.

As noted above, all of the foregoing embodiments (MRP-β nucleic acids, host cells, MRP-β protein and antibodies thereto) are useful to characterize MRP-β biological function. Natural production of the MRP-β polypeptide also in untransformed mammalian body tissues likely endows the cell with active transport or secretion properties, by which a cell metabolite, secretion product, or biological response mediator is imported or, more likely, released from the producing cell. Thus, the normal physiological function of MRP-β may be the transport of one or more lipids, or substances comprising a moiety with lipid character, across the cell membrane. For example and without being limited by speculation, MRP-β may transport a bile acid or a steroid hormone or precursor thereof. Alternatively, MRP-β may mediate cellular uptake of short-chain fatty acids as an energy source. Thus, MRP-β may transport naturally- or synthetically-sourced substances, including chemotherapeutic drugs, that have salient physical or chemical properties in common with the natural transport substrate(s). The MRP-β expressing host cells provided herein thus are expected to facilitate investigation and characterization of substances, including cytotoxins, that are subject to MRP-β mediated transport.

Classical radioassay and/or metabolic radiolabelling techniques can be adapted routinely to screening known cell metabolites and/or secretion products to determine which may be a natural MRP-β transported substrate. Phospholipids, glycolipids, extracellular matrix precursors, endocrine hormones, proinflammatory steroids, bile acids, metabolites of any of the foregoing, and the like can be radiolabeled by incorporation of $^3$H, $^{35}$S, $^{14}$C or $^{32}$P according to standard techniques. Uptake, sequestration and/or efflux of radiolabeled candidate substrates can be monitored by assessing changes in radioactivity levels (e.g., by scintillation counting, auto-radiography or a similar technique) in MRP-β host cells; in culture medium conditioned by MRP-β host cells; or, as desired, in any appropriate subcellular fraction (e.g., a scintillation fraction) prepared conventionally from MRP-β host cells. Identification of one or more natural substrates for MRP-β may be relevant to the design or selection of potential MRP-β modulators as described below.

Any conventional technique for monitoring cellular susceptibility to a cytotoxin of interest, or for monitoring intracellular accumulation, sequestration or efflux thereof, can be adapted with no more than routine experimentation to characterization of the biological (e.g., transport) properties of MRP-β. Thus, the chemosensitivity testing, accumulation and efflux assays summarized in Cole et al. (1994), 54 *Cancer Res. Cancer Res.* 5902–5910 can be used for characterization of MRP-β export of drugs and/or toxins such as (but not limited to) doxorubicin, vincristine, colchicine, VP-16, vinblastine, verapamil, mitoxantrone, taxol, Cyclosporin A, quinidine, progesterone, tamoxifen, epirubicin, daunorubicin, MX2, and heavy metal ions such as arsenite, arsenate, antimony tartrate, antimonate, and cadmium, whether alone or in any combination thereof. Additional suitable characterization assays include the fluorescence cell sorting techniques disclosed in Krishan (1990), 33 Meth. Cell Biol. 491–500 and in Engel et al. (1996), U.S. Pat. No. 5,556,856 (both incorporated herein by reference), which capitalize on the fluorescent properties of daunorubicin. Another suitable assay is set forth in Zelle et al. (1996), U.S. Pat. No. 5,543,423 (incorporated herein by reference), and is based on assessment of cellular uptake of vital dyes following a period of exposure to a potentially exportable cytotoxin. Additional published assays are summarized in Piwnica-Worns (1995), U.S. Pat. No. 5,403,574 (incorporated herein by reference), and are based on uptake and/or efflux of fluorescent dyes, such as rhodamine. If desired, the rapid yeast cell-growth monitoring assay set forth in Ruetz et al. (1996), 271 *J. Biol. Chem.* 41544160, also can be applied.

Additional therapeutic methods for treating abnormalities or disease states associated with MRP-β, especially with the occurrence of a multidrug-resistance phenotype, are based on the identification and use of modulators, preferably inhibitors, that affect MRP-β gene activation or expression, transcript stability, polypeptide production, post-translational processing, insertion into cellular phospholipid membranes, stabilization and/or biological function, especially transport function. A candidate substance that detectably affects (products a fluctuation in) any of the foregoing MRP-β parameters is identified herein as an MRP-β modulator. Thus, for example, a candidate that interferes with host cell resistance to a cytotoxin is identified herein as a preferred inhibitory modulator (inhibitor) of MRP-β. Candidate sustances to be subjected to screening and/or identification methods described herein available or can be produced by routine adaptations of teachings set forth in *Intelligent Drug Design, A Nature Supplement,* 384 *Nature,* Suppl. to No. 6604 (1996). Additional exemplary sources of candidate MRP modulators are taught in Agrafiotis et al. (1995), U.S. Pat. No. 5,463,564; Zambias et al. (1996), PCT Publ. No. WO96/22529; Hogan et al. (1996), PCT Publ. No. WO96/12482; Hogan (1995), PCT Publ. Nos. WO95/32184 and WO95/18972; and, Beutel et al. (1995), PCT Publ. No. WO95/27072. Preferred candidate substances are small molecules, e.g., elements of a combinatorial chemistry or natural products library or pharmacopoeia. Currently, multidrug-resistant derivatives of the MCF-7 cell line, or MCF-7 host cells displaying a vector-derived, cell surface MRP-β polypeptide, are preferred herein for the identification of modulators of MRP-β. Any of the above-mentioned assays can be used for the present purpose, including high-throughput cell survival assays that monitor whether the present MRP-β expressing MCF-7 cells survive exposure to cytotoxin levels at which non-resistant cells normally succumb. For example, survival of MRP-β expressing host cells can be compared to survival of mock transfected MCF-7 cells at equivalent cytotoxin concentrations.

As mentioned previously herein, several inhibitors or antagonists of the known mammalian ABC Transporter Proteins, P-glycoprotein and MRP, have been disclosed. An inhibitor or antagonist that achieves complete interference with gene expression, polypeptide production and/or function effectively reverses the multidrug resistance phenotype, restoring cellular vulnerability to the cytotoxic effects of an otherwise exported chemotherapeutic drug. An inhibitor or antagonist that achieves partial interference also can be considered beneficial clinically, in that partial interference with drug export function "attenuates" or reduces penetrance of the multidrug resistance phenotype. Upon treatment with a partial inhibitor, cellular vulnerability to cytotoxins is increased, albeit not fully restored. Such substances are commonly referred to in the art as "MDR reversal agents" or "chemosensitizing agents." Powell et al. (1996), U.S. Pat. Nos. 5,561,141 and 5,550,149; Powell et al. (1995), U.S. Pat. No. 5,387,685; Engel et al. (1996), U.S. Pat. No. 5,556,856; Zelle et al. (1996), U.S. Pat. No. 5,543,423; Sunkara (1996), U.S. Pat. No. 5,523,304; Sunkara et al (1993), U.S. Pat. Nos. 5,190,957 and 5,182,293; Sarkadi et al. (1995), PCT Publ. WO 95/31474; Piwnica-Worms (1995), U.S. Pat. No. 5,403,574; Hait et al. (1992), U.S. Pat. No. 5,104,856. Little structural similarity has been observed between the known classes of MDR reversal agents, or between reversal agents and exported cytotoxic drugs. Thus, high through-put screening, e.g., of naturally-sourced or synthetic chemicals in a pharmacopoeia or combinatorial library, was required to identify each currently known MDR reversal agent. Furthermore, the majority of known MDR reversal agents are specific inhibitors of either P-glycoprotein or of MRP: little to no cross-inhibition has been observed. Thus, it is expected that empirical screening will be required, for the identification of one or more modulators, preferably inhibitors, of MRP-β. Exemplary identification or screening protocols are referenced herein and appear herein in EXAMPLES 4 and 5.

All modulators of MRP-β, including partial modulators, that are identified through practice of the above-described methods, or routine modifications thereof, are considered to be within the scope of the present invention. Small molecule modulators are preferred. Inhibitory modulators (inhibitors) are especially contemplated herein. For therapeutic administration purposes, a modulator of the present invention can be administered to an individual as a pharmaceutically acceptable salt or derivative. Further, the present modulator can be formulated with any pharmaceutically acceptable carrier, excipient, adjuvant or vehicle. Appropriate pharmaceutically acceptable salts, derivatives, carriers, excipients, adjuvants and vehicles are as disclosed in Zelle et al. (1996), U.S. Pat. No. 5,543,423 (which is incorporated herein by reference) or can be produced or selected by routine modifications thereof.

The present MRP-β modulator accordingly can be used to mitigate severity of, up to an including to abrogate, any phenotype associated with an abnormality affecting MRP-β. That is, the present modulator may be used to treat or palliate any disease or condition affecting the health status of an individual, such as a human, that arises from the MRP-β abnormality. The modulator also may be administered prophylactically, to avert or delay the onset of a deleterious phenotype associated with MRP-β dysfunction. In particular, the present NW-0 modulator is useful to attenuate a multidrug-resistance phenotype attributable in whole or in part to MRP-β gene abnormality, gene expression, transcript stabilization, or polypeptide production, processing, stability or biological function, e.g., in transformed cells in situ in mammalian body tissue. Preferred inhibitory modulators make possible novel methods, for example, of potentiating chemotherapy to eradicate multidrug-resistant transformed cells from the body of a mammal. As with the antisense pharmaceutical composition method discussed herein, the effectiveness of chemotherapy is enhanced by restoring or improving vulnerability of the transformed cells to the cytotoxic effects of a chemotherapeutic drug that otherwise would be ejected from the cell. The present, modulator-based method involves administering the modulator alone or as an adjuvant to the desired chemotherapeutic drug, to an individual afflicted with a multidrug-resistant tumor, e.g., a carcinoma, sarcoma, leukemia, lymphoma or lymphosarcoma. The chemotherapeutic drug and MRP-β modulator may be administered concurrently or in any order, and can be separated by a time interval sufficient to allow uptake of either compound by the transformed cells to be eradicated. If desired, the present modulator can be administered alone or in a cocktail, combined with one or more known MDR reversal agents (e.g., agents that affect MRP or P-glycoprotein).

Preferably, the modulator is administered to the individual sufficiently in advance of administration of the chemotherapeutic drug to allow the modulator to permeate the individual's tissues, especially tissue comprising the transformed cells to be eradicated; to be internalized by transformed cells; and to impair MRP-β mediated cytotoxin sequestration or efflux. The time interval required can be determined by routine pharmacokinetic means, and should be expected to vary with age, weight, sex, lean tissue content, and health status of the individual, as well as with size and body compartment location of the population of multidrug-resistant transformed cells to be eradicated. Similar parameters should be considered in selecting a route of administration of the modulator. Thus, the modulator may be administered locally or systemically, preferably by a parenteral route. It can be administered intravenously, intraperitoneally, retroperitoneally, intracisternally, intramuscularly, subcutaneously, topically, intraorbitally, intranasally or by inhalation, optionally in a dispersable or controlled release excipient. One or several doses may be administered as appropriate to achieve uptake of a sufficient amount of the present modulator to produce an attenuation of multidrug-resistance phenotype in the transformed cells to be eradicated by chemotherapy. As a result of therapeutic intervention with an MRP-β modulator (preferably, an inhibitory modulator), penetrance of an abnormal or deleterious phenotype (generally, but not limited to, a multidrug resistance phenotype) is attenuated, even abrogated, in the treated individual. The overall dosage and administration protocol for treatment with the present modulator may be designed and optimized by the clinical practitioner through the application of routine clinical skill.

Practice of the invention will be still more fully understood from the following EXAMPLES, which are presented solely to illustrate principles and operation of the invention, and should not be construed as limiting scope of the invention in any way.

EXAMPLE 1

Isolation and cloning of fill-length MRP-β cDNA

A unique fragment (SEQ ID No: 3) of the novel MRP-β gene was identified by computer-assisted screening of a nucleic acid database corresponding to a human endothelial cell expression library. The library was prepared using cellular RNA transcripts produced in human microvascular endothelial cells (HUMVEC) isolated from breast tissue and maintained in primary culture in the presence of a commercially available extracellular matrix composition (Matrigel), and in the presence of appropriate growth and differentiation factors (e.g., vascular endothelial cell growth factor (VEGF)). These conditions had previously been shown to preserve cell viability and substantially differentiated phenotype in vitro.

Figure 1D:
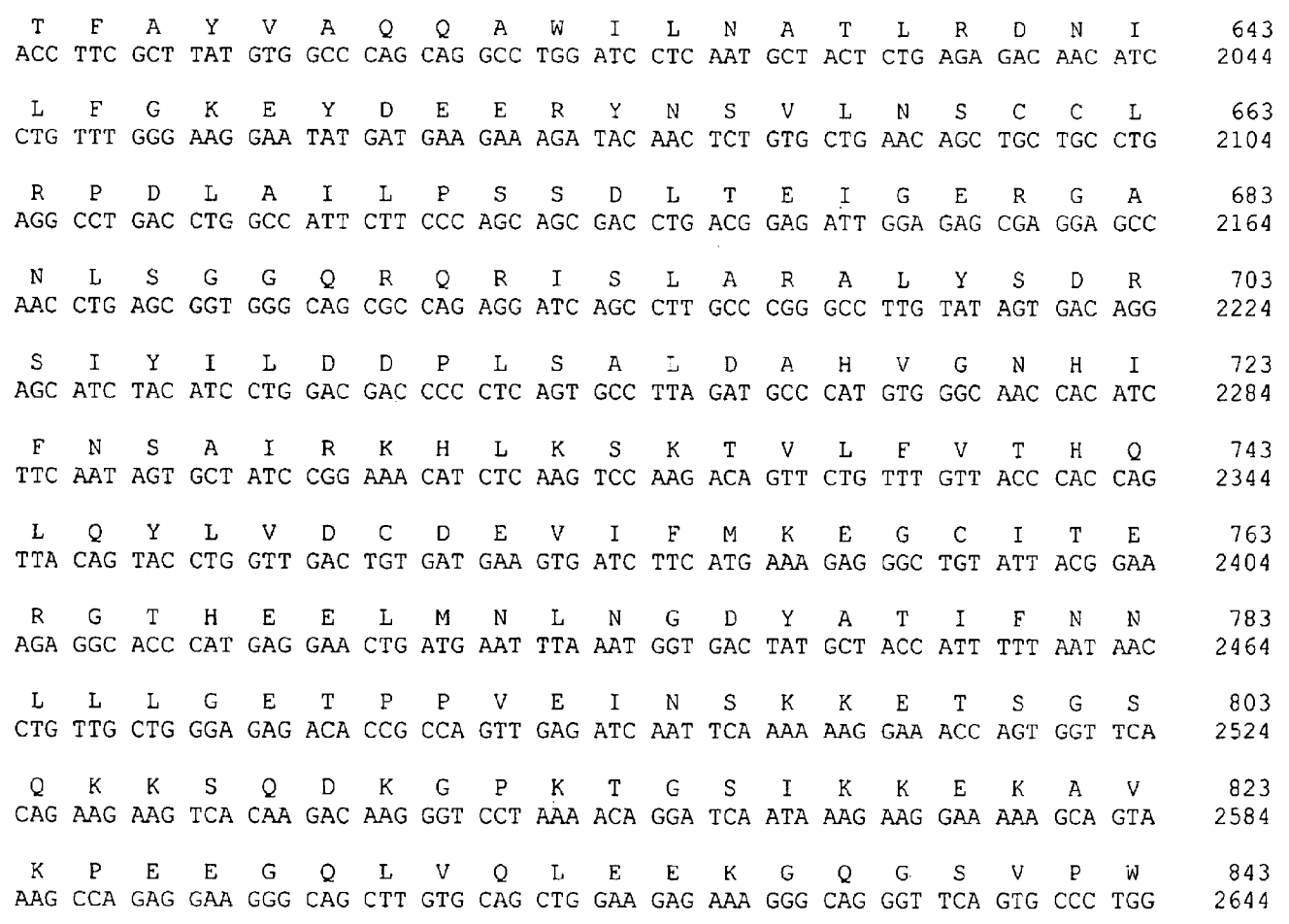

A nucleic acid probe corresponding to the SEQ ID No: 3 unique fragment was prepared by conventional techniques. This probe was used for hybridization screening of the HUMVEC expression library for the presence of MRP-β cDNAs. This procedure yielded an MRP-β cDNA (residues 67–4847 FIG. 1A-G and SEQ ID No: 1), 4.78 kb (kilobases) in length. The clone comprising this cDNA insert has been designated fohd013a05m and deposited with the American Type Culture Collection. Two independent cDNA clones comprising approximately 60 residues upstream (5') from the fohd013a05m MRP-β insert were isolated by hybridization screening of human brain and liver cDNA libraries with a nucleic acid probe corresponding approximately to the 5' 0.5 kb of the fohd013a05m MRP-β insert. This probe was prepared by isolating an approximately 0.5 kb SacI fragment from fohd013a05m. The cDNA sequence presented in SEQ ID No: 1 comprises the sequence of the fohd013a05m MRP-β insert and the sequence of an additional 66 upstream (5') nucleotides. The open reading frame (ORF) of the SEQ ID No: 1 cDNA encodes an MRP-β polypeptide (SEQ ID No: 2) 1437 amino acid residues in length and in addition, includes a 0.42 kb 3' untranslated region. The ORF start site indicated in SEQ ID No: 1 (at nucleotides 116–118 of SEQ ID No: I) is the first in-frame ATG codon downstream from the TGA stop codon at nucleotides 23–25 of SEQ ID No: 1.

EXAMPLE 2

Correlation of MRP-β expression level with multidrug-resistance phenotype.

Involvement of the present novel MRP-β gene in the acquisition or maintenance of a multidrug-resistance phenotype has been confirmed by comparing the level of MRP-β gene expression in immortalized, transformed cells (wild-type or parent cells) that have not acquired the property of multidrug-resistance with the level in a multidrug-resistant derivative of the parent cell population. One set of exemplary parent and multidrug-resistant derivative cell lines are described in Mirsky et al. (1987), 47 *Cancer Res.* 2594–2598 (parent and multidrug-resistant (MDR) derivative of the H69 human small cell lung carcinoma line). Additional exemplary parent and multidrug-resistant derivative lines are described in Slapak et al. (1994), 84 Bloo 3113–3121 (parent and MDR derivative of the U937 human myeloid leukemia line); Batist et al. (1986), 261 *J. Biol. Chem.* 15544–15549 (parent and MDR derivative of the MCF-7 human breast adenocarciinoma line); March et al. (1986), 46 *Cancer Res.* 4053–4057 (parent and MDR derivative of the HL-60 human promyelocytic leukemia line); and, Hamilton et al. (1984), 11 *Sem. Oncol.* 285–298 (parent and MDR derivative of the A2780 human ovarian carcinoma line). Each of the foregoing references is incorporated herein by reference. To demonstrate correlation between MRP-β gene expression and multidrug-resistance phenotype, parental (wild-type) and adriamycin-selected multidrug resistant MCF-7 cells were cultured to confluency under standard cell culture conditions and treated to release expressed nucleic acid transcripts, which were subjected to Northern blot analysis.

Preparation of cellular RNA. Expressed nucleic acids were isolated from the exemplary parental and resistant MCF-7 cells using components of the Qiagen, Inc. RNeasy Total RNA kit, generally as in the Qiagen, Inc. *RNeasy Handbook* (1995). Kit components include spin columns, collection tubes, lysis buffer, wash buffer and RNAse free water. Expressed nucleic acid extracts were prepared by suspending cells in lysis buffer supplemented with 2-mercaptoethanol and passage of the resulting mixture through a Qiagen, Inc. Qiashredder homogenization column. RNA was purified from the resulting lysate using a Qiagen, Inc. RNeasy column supplied with the kit. The lysate was loaded onto the RNeasy colum, washed and RNA was eluted generally as described in the *RNeasy Handbook.*

Electrophoretic Resolution of Expressed RNAs. Agarose-formaldehyde slab gels (1.0–2.5% agarose) were prepared and cast according to standard techniques. RNA samples (10–30 μg total RNA or 1–3 μg PolyA(+) RNA) were combined with denaturing bromophenol blue sample buffer, loaded onto the gel and subjected to electrophoresis by passage of 100 volts through the gel chamber for about 3 hours or until the bromophenol blue dye front had migrated about 10 cm into the gel. A photograph of the resolved gel was obtained prior to transfer of resolved RNAs to nylon.

Replica Transfer of Resolved RNAs to Nylon. The gel comprising resolved cellular MRP-β transcript was prepared for transfer by soaking in 0.05 N NaOH, 0.15 M NaCl for 20–30 minutes, followed by neutralization in 0.1 M Tris pH 7.5, 0.15 M NaCl for 30 minutes. RNA contents of the neutralization gel were then transferred to a nylon membrane using a Posiblot apparatus (Stratagene, Inc.). Transfer was allowed to proceed for 1 hour, following which the transferred, resolved RNAs were crosslinked to the membrane using UV light generated by a Stratalinker apparatus (Stratagene, Inc.). The location of resolved RNAs on the membrane was visualized by staining with methylene blue. The positions of the RNA ladder, 18S, and 28S ribosomal RNAs were marked on a photograph taken of the stained membrane, which was then destained according to standard procedure.

Preparation of detectably labeled MRP-β Probe. A unique fragment (e.g., SEQ ID No: 3) of the MRP-β cDNA was used for the preparation of a radiolabeled hybridization probe for visualizing the electrophoretically resolved, full-length MRP-β transcript expressed in parent (wild-type) and MDR MCF-7 cells. The probe was prepared using the Stratagene, Inc. Prime It-RmT Primer Labeling Kit, generally according to the protocol supplied by the manufacturer (see also Feinberg et al. (1984) 137 *Anal. Biochem.* 266–267 and Feinberg et al. (1983), 132 *Anal. Biochem.* 6–13). Kit components include control DNA, Magenta thermostable DNA polymerase, stop mix, and dehydrated single-use reaction mixtures comprising random primers, nucleotides, buffer and cofactors required by the polymerase. To prepare the probe, 50 ng MRP-βDNA (e.g., cDNA insert comprising SEQ ID No: 3) in aqueous solution was added to a kit single-use reaction mixture and boiled to ensure denaturation. To obtain incorporation of at least $10^6$ cpm/μL, 5 μL [α-$^{32}$P]dCTP (6000 Ci/mmol) was added to the mixture, followed by 3 mL Magenta polymerase (4U/uL). Probe synthesis was conducted at 37° C. for 10 minutes, then stopped by the addition of 2 μL stop mix. To reduce background, the labeled probe was purified using a chromaspin TE-10 column prior to use for hybridization.

Hybridization. Prior to contact with the radiolabeled probe, the nylon membrane comprising crosslinked, electrophoretically resolved MCF-7 cellular transcripts was prehybridized for 20 minutes at 65° C. in 10 mL Rapid-hyb solution available from Amersham, Inc. The prepared probe was boiled for 5 minutes to ensure denaturation, and added to an additional 10 mL Rapid-Hyb solution. The prehybridization solution was exchanged for probe solution, and the probe was allowed to hybridize to membrane-bound transcripts for 2 hours at 65° C. Excess, unhybridized probe was removed by washing the membrane in 2×SSC, 0.1% SDS for 20 minutes, either at room temperature or at 42° C. Thereafter, the membrane was washed in 0.1×SSC, 0.1% SDS for 20 min. at 65° C. The 65° C. wash step was repeated if necessary to obtain a satisfactory signal-to-background ratio as assessed by geiger counter. Results were visualized by exposure to X-ray film according to standard procedures. Thereafter, MRP-β probe was stripped by addition of a boiling solution of 0.5% (w/v) SDS (0.1×SSC, 0.1% SDS also can be used as a stripping solution). Significance of the MRP-0 results were verified by rehybridization of the membrane with a probe specific for the transcript of a conventionally used housekeeping or structural gene (e.g., Ef-TU or actin).

Results. A single 6 kb transcript was visualized by the MRP-β probe in both wild-type and MDR MCF-7 cellular RNA. A significantly elevated level of the MRP-β transcript was observed in the MDR derivative cell line, which is reported in Batist et al. (1986) to be 192-fold more resistant to adriamycin than the parental (wild-type) MCF-7 human breast adenocarcinoma cell line. Consistent results showing elevated levels of MRP-β gene expression were observed in comparison studies of parental and MDR derivative cell lines established from human ovarian carcinoma (A2780; Hamilton et al. (1984)) and human leukemias (HL-60; March et al. (1986), and U937; Slapak et al. (1994)). Thus, MRP-β gene expression level correlates with the acquisition of a multidrug-resistance phenotype, rather than with the body tissue type in which a particular tumor arises.

EXAMPLE 3

Expression of MRP-β in Mammalian Body Tissues

As noted above, a clearly detectable baseline level of MRP-β gene expression was observed even in wild-type tumor cell lines. To establish whether this baseline expression correlates with tumorigenesis, the above-described radiolabeled MRP-βprobe was hybridized to commercially available human multiple tissue Northern (MTN) blots (Clontech, Inc.), generally according to the manufacturer's directions and the procedure described above in EXAMPLE 2. Tissues from which polyA(+)RNA was analyzed included heart, brain, placenta, lung, liver, skeletal muscle, kidney, pancreas, spleen, thymus, prostate, testis, ovary, small intestine, colon (mucosal lining) and peripheral blood leukocyte.

Results. Clearly detectable baseline expression of a 6 kb MRP-β transcript was observed in substantially all normal human body tissues surveyed, with the highest expression level being observed in heart tissue. The survey samples represent expressed RNAs isolated from lysates of whole tissue, rather than from specific cell types characteristic of one or more body tissues. Taken together with the isolation of MRP-β cDNAs from a HUMVEC expression library (described in EXAMPLE 1), the present MTN survey data is consistent with substantially ubiquitous baseline expression of MRP-β in vasculature or microvasculature.

EXAMPLE 4

Confirmation that MRP-β expression is sufficient to confer a survival advantage on cells exposed to a cytotoxic agent Host cells stably transfected with an MRP-β expression vector as described herein are expected to gain a significant survival advantage, relative to source (untransfected) or control (antisense transfected) cells. To establish this survival advantage, triplicate cultures of MRP-β host cells, control cells and source cells (e.g., MCF-7 human breast adenocarcinoma cells) are generated in 24-well cell culture plates. Once the cultures have attained at least 80% confluency, lethal or sub-lethal amounts of a cytotoxin (e.g., adriamycin, bisantrene) are added to each well. After a sufficient period of time for cytotoxic effects to be manifested (e.g., 16–24 hours in culture), culture media comprising the cytotoxic drug are aspirated or otherwise removed, and cells are stained with a vital dye such as Trypan blue. Which commercially available vital dye is used in this procedure is a matter of choice; thus, sulforodoamine B (see Powell et al. (1990), U.S. Pat. No. 5,550,149) could be used in lieu of Trypan blue. The number of cells that remain viable (e.g., capable of excluding the dye) are counted using a hemocytometer, flow cytometer or other appropriate device.

Expected Results, MRP-β expressing host cells are expected to acquire the capability of surviving exposure to otherwise lethal amounts of a cytotoxin, such as adriamycin or bisantrene. Analysis of the differential between toxin levels that are lethal to source or control cells, and that which is lethal to MRP-β host cells, is expected to provide a predictive index of the recalcitrance of MRP-β expressing transformed cells in situ to chemotherapy. Repetition of this cytotoxicity assay with additional toxins (e.g., environmentally or occupationally derived toxins, metabolites or chemotherapeutic drugs) is expected to elucidate the nature of substances exportable or sequestrable by MRP-β and to uncover specific differences between the characteristics of substrates transported by MRP-β and those transported by known ATP Transporter Protein superfamily members such as P-glycoprotein and/or MRP.

Screening for a modulator of MRP-β. The present cytotoxicity assay can be adapted routinely to provide a rapid assay for screening candidate modulators of MRP-β. In this adaptation, host cell cultures are incubated in the presence of a toxin to which MRP-β expression confers a survival advantage. The level of toxin exposure is sub-lethal to host cells but lethal to source cells or control cells. Candidate MRP-β modulators (e.g., inhibitors) are added to the cell cultures, which are incubated for a sufficiently further period of time for cytotoxicity to be manifested (e.g., 16–24 hours). A candidate that attenuates or abrogates the host cells' survival advantage is identified as an MRP-β inhibitor. Guidelines for this adaptation of the present cytotoxicity assay may be found in Powell et al. (1996), U.S. Pat. No. 5,550,149. Candidate MRP-β modulators may be selected from any appropriate source, such as a pharmacopeia of natural or synthetic substances, combinatorial chemistry library, phage display epitope library, or the like. Appropriate sources are available or can be produced by routine adaptations of teachings set forth in *Intelligent Drug Design, A Nature SupplemenL* 384 *Nature*, Suppl. to No. 6604 (1996). Additional exemplary sources of candidate MRP-β modulators are taught in Agrafiotis et al. (1995), U.S. Pat. No. 5,463,564; Zambias et al. (1996), PCT Publ. No. WO96/22529; Hogan et al. (1996), PCT Publ. No. WO96/12482; Hogan (1995), PCT Publ. Nos. WO95/32184 and WO95/18972; and, Beutel et al. (1995), PCT Publ. No. WO95/27072.

EXAMPLE 5

Assessment of MRP-β Mediated Drug Efflux

Without being limited by speculation, it is likely that MRP-β confers the above-described survival advantage by mediating sequestration or efflux of one or more cytotoxins. That is, it is likely that MRP-β is a member of the ABC Transporter Protein superfamily that carries out an export function. However, routine empirical testing is required to confirm whether MRP-β exports one or more toxic substances, or imports one or more nutrients or energy sources, such as sugars or fatty acids of dietary or other metabolic origin. A number of conventional protocols can be practiced, with such routine modifications as may be deemed appropriate by the practitioner, to establish whether MRP-β mediates toxin export. A presently preferred technique capitalizes on the fluorescent properties of anthracycline toxins (including adriamycin (doxorubicin) and daunomycin), such that toxin accumulation and/or efflux from MRP-β expressing host cells can be monitored by fluorescence histochemistry or, preferably, by fluorescence-activated flow cytometry. An example of this technique is described in Krishan (1990), 33 Meth. Cell Biol, 491–500, incorporated herein by reference.

Fluorescent labeling. Viable MRP-β host cells (at least 10,000) are suspended in culture medium in the sampling cuvette of a flow cytometer, such as the EPICS 753 apparatus (Coulter Electronics, Inc.) equipped with an argon laser for fluorophore excitation at 488 nm, and a photomultiplier (e.g., MDADS II data acquisition apparatus) for detection of 530 nm emissions. The cuvette is maintained at 37° C., and adriamycin or daunomycin are added to a final concentration of 1–3 μM prior to cell sorting. Two-parameter histograms are generated based on cellular fluorescence and incubation time (typically 30 to 60 minutes) in the presence of the fluorescent toxin.

Expected results. MRP-β host cells are expected to internalize and/or retain significantly lower levels of adriamycin or daunomycin than source cells or control cells.

Screening for a modulator of MRP-β. The above drug efflux assay can be adapted routinely to provide a rapid assay for screening candidate modulators of MRP-β. In this adaptation, a candidate MRP-β modulator is added to the cuvette during the fluorophore uptake incubation. A candidate that attenuates or abrogates the host cells' capacity for fluorophore efflux is identified as an MRP-β inhibitor. Guidelines for this adaptation may be found in Krishan (1990), 33 Meth. Cell Biol. 491–500). Candidate MRP-β modulators may be selected from any appropriate source, such as the sources mentioned in EXAMPLE 4.

Equivalents

The invention may be embodied in other specific forms without departing from the spirit or essential characteristics thereof. For example, the invention may be embodied in one or more variants, e.g., deletion, addition or substitution variants, of the nucleic acid and/or protein sequences disclosed herein, such as may be produced routinely by mutagenesis or other conventional molecular engineering and biosynthetic production techniques. Specifically, the invention may be embodied in any variant, whether biosynthetically produced or isolated from a natural source, the expression or overexpression of which endows a mammalian cell with a multidrug-resistance phenotype. More specifically, the invention may be embodied in a variant which, when expressed or overexpressed, endows a mammalian cell with resistance to the cytotoxic effects of MRP-β transportable drugs. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of identifying an inhibitor of MRP-β, comprising the steps of:
 (a) contacting a cell with a candidate inhibitor of MRP-β;
 (b) assaying the level of expression of the MRP-β nucleic acid molecule set forth as SEQ ID No: 1 in said cell, wherein a detectable decrease in said level indicates that said candidate modulator inhibitor is an MRP-β inhibitor, thereby identifying an MRP-β inhibitor.

2. A method of identifying an inhibitor of MRP-β, comprising the steps of:
 (a) contacting a cell with a substrate exported or sequestered by MRP-β, said cell expressing a vector-derived MRP-β polypeptide, the amino acid sequence of which shares at least 90% sequence identity with SEQ ID No: 2, wherein said MRP-β functions to transport, expel, or sequester substances from an intracellular milieu, and wherein;
 (b) contacting said cell with a candidate modulator inhibitor of MRP-β;
 (c) assaying for a detectable decrease in export or sequestration of said substrate,
 wherein a detectable decrease in said export or sequestration indicates that said candidate inhibitor is an MRP-β m inhibitor, thereby identifying an MRP-β inhibitor.

3. A method of identifying a inhibitor of MRP-β, comprising the steps of:
 (a) contacting a cell with a cytotoxin exported or sequestered by MRP-β, said cell expressing a vector-derived MRP-β polypeptide, the amino acid sequence of which shares at least 90% sequence identity with SEQ ID No: 2, wherein said MRP-β functions to transport, expel, or sequester substances from an intracellular milieu;
 (b) contacting said cell with a candidate modulator inhibitor of MRP-β;
 (c) assaying survival of said cell,
 wherein a detectable decrease in said survival indicates that said candidate inhibitor is an MRP-β inhibitor, thereby identifying an MRP-β inhibitor.

4. A method of identifying an inhibitor of MRP-β, comprising the steps of:

(a) contacting a cell with a candidate inhibitor;

(b) assaying the level of expression of the MRP-β polypeptide set forth as SEQ ID No: 2 in said cell wherein said MRP-β functions to transport, expel, or sequester substances from an intracellular milieu, wherein a detectable decrease in said level indicates that said candidate inhibitor is an MRP-β inhibitor, thereby identifying an MRP-β inhibitor.

5. A method of identifying an inhibitor of MRP-β, comprising the steps of:

(a) contacting a cell with a substrate exported or sequestered by WP-0, said cell expressing a vector-derived MRP-β polypeptide encoded by a nucleic acid molecule which hybridizes under conditions of hybridization in 0.5M NaHPO$_4$ at 65° C. followed by washing in 0.1×SSC at 68° C. to a complement of the nucleic acid molecule having the sequence of SEQ ID No: 1, wherein said MRP-β polypeptide functions to transport, expel, or sequester substances from an intracellular milieu;

(b) contacting said cell with a candidate inhibitor of MRP-β;

(c) assaying for a detectable decrease in export or sequestration of said substrate, wherein a detectable decrease in said export or sequestration indicates that said candidate inhibitor is an MRP-β inhibitor, thereby identifying an MRP-β inhibitor.

6. A method of identifying an inhibitor of MRP-β, comprising the steps of:

(a) contacting a cell with a substrate exported or sequestered by MRP-β, said cell expressing a vector-derived MRP-β polypeptide encoded the nucleic acid molecule having the sequence of SEQ ID No: 1;

(b) contacting said cell with a candidate modulator inhibitor of MRP-β;

(c) assaying for a detectable decrease in export or sequestration of said substrate, wherein a detectable decrease in said export or sequestration indicates that said candidate inhibitor is an MRP-β inhibitor, thereby identifying an MRP-β inhibitor.

7. A method of identifying an inhibitor of MRP-β, comprising the steps of:

(a) contacting a cell with a substrate exported or sequestered by MRP-β, said cell expressing a vector-derived MRP-β polypeptide by the DNA insert of the plasmid deposited as ATCC Deposit No. 94809;

(b) contacting said cell with a candidate inhibitor of MRP-β;

(c) assaying for a detectable decrease in export or sequestration of said substrate, wherein a detectable decrease in said export or sequestration indicates that said candidate inhibitor is an MRP-β inhibitor, thereby identifying an MRP-β inhibitor.

8. A method of identifying an inhibitor of MRP-β, comprising the steps of:

(a) contacting a cell with a cytotoxin exported or sequestered by MRP-β said cell is expressing a vector-derived MRP-β polypeptide encoded by a nucleic acid molecule which hybridizes under conditions of hybridization in 0.5M NaHPO$_4$ at 65° C. followed by washing in 0.1×SSC at 68° C. to a complement of the nucleic acid molecule having the sequence of SEQ ID No: 1, wherein said MRP-(3 functions to transport, expel, or sequester substances from an intracellular milieu, and wherein;

(b) contacting said cell with a candidate inhibitor of MRP-β;

(c) assaying survival of said cell, wherein a detectable decrease in said survival indicates that said candidate inhibitor is an MRP-β inhibitor, thereby identifying an MRP-β inhibitor.

9. A method of identifying an inhibitor of MRP-β, comprising the steps of:

(a) contacting a cell with a cytotoxin exported or sequestered by MRP-β said cell expressing a vector-derived MRP-D polypeptide encoded the nucleic acid molecule having the sequence of SEQ ID No: 1;

(b) contacting said cell with a candidate inhibitor of MRP-β;

(c) assaying survival of said cell, wherein a detectable decrease in said survival indicates that said candidate inhibitor is an MRP-β inhibitor, thereby identifying an MRP-βinhibitor.

10. A method of identifying an inhibitor of MRP-β, comprising the steps of:

(a) contacting a cell with a cytotoxin exported or sequestered by MRP-β, said cell expressing a vector-derived MRP-β polypeptide by the DNA insert of the plasmid deposited as ATCC Deposit No. 94809;

(b) contacting said cell with a candidate inhibitor of MRP-β;

(c) assaying survival of said cell, wherein a detectable decrease in said survival indicates that said candidate inhibitor is an MRP-β inhibitor, thereby identifying an MRP-β inhibitor.

11. The method of claim 2 or claim 3, wherein the amino acid sequence of the vector-derived MRP-β polypeptide shares at least 95% sequence identity with the amino acid sequence of SEQ ID No: 2.

12. The method of any one of claims 2 and 5–7, wherein the substrate is a cytotoxin.

13. The method of any one of claims 2 3 and 5–10 wherein MRP-β expression confers a survival advantage on said cell.

14. The method of any one of claims 2–3 and 5–10, wherein the cell expresses a cell surface MRP-β polypeptide.

15. The method of any one of claims 1–3 and 5–10, wherein the cell is a eukaryotic cell.

16. The method of any one of claims 1–3 and 5–10, wherein the cell is a yeast or mammalian cell.

17. The method of any one of claims 1–3 and 5–10, wherein the cell is a human cell.

18. The method of any one of claims 1–3 and 5–10, wherein the cell is a MCF-7 cell.

19. The method of claim 1, wherein assaying the level of MRP-β comprises assaying the amount or rate of production of MRP-β nucleic acid molecule.

20. The method of claim 4, wherein assaying the level of MRP-β comprises assaying the amount or rate of production of MRP-β polypeptide is in said cell.

21. The method of any one of claims 1–3 and 5–10, wherein the candidate inhibitor is contacted with the cell prior to, concomitantly with, or following exposure to the substrate.

22. The method of any one of claims 1–3, wherein the candidate inhibitor is selected from the group consisting of a natural metabolite, a synthetic chemical, a synthetic metabolite, a toxin, an antibiotics, an element of a combinatorial chemistry library, an element of a nucleotide library, an element of a peptide library, a naturally sourced chemical, a naturally sourced cell secretion product, a cell lysate.

23. The method of any one of claims 1–3, wherein the candidate inhibitor is a small molecule.

24. The method of claim 2 or 3, wherein the amino acid sequence of the vector-derived MRP-β polypeptide comprises the amino acid sequence of SEQ ID No: 2.

* * * * *